(12) United States Patent
An et al.

(10) Patent No.: US 11,639,531 B2
(45) Date of Patent: May 2, 2023

(54) COMPOSITION, KIT, AND METHOD FOR DIAGNOSIS AND TREATMENT OF TAXANE ANTICANCER AGENT-RESISTANT CANCER

(71) Applicant: SUNGKWANG MEDICAL FOUNDATION, Seoul (KR)

(72) Inventors: Hee Jung An, Seoul (KR); Tae Heon Kim, Seongnam-si (KR); Hae Youn Kang, Seoul (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 115 days.

(21) Appl. No.: 17/255,235

(22) PCT Filed: Mar. 20, 2019

(86) PCT No.: PCT/KR2019/003220
§ 371 (c)(1),
(2) Date: Dec. 22, 2020

(87) PCT Pub. No.: WO2019/245135
PCT Pub. Date: Dec. 26, 2019

(65) Prior Publication Data
US 2022/0119888 A1    Apr. 21, 2022

(30) Foreign Application Priority Data

Jun. 22, 2018  (KR) .................. KR10-2018-0072219

(51) Int. Cl.
*A61K 31/7088*    (2006.01)
*C12N 15/113*    (2010.01)
*C12Q 1/6886*    (2018.01)

(52) U.S. Cl.
CPC ........ *C12Q 1/6886* (2013.01); *A61K 31/7088* (2013.01); *C12N 15/113* (2013.01); *C12N 2310/141* (2013.01); *C12N 2320/31* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 9,915,661 | B2 | 3/2018 | An et al. | |
|---|---|---|---|---|
| 2013/0121912 | A1* | 5/2013 | Yao .................... | A61K 31/7105 428/34.1 |

FOREIGN PATENT DOCUMENTS

KR    10-1816119 B1    1/2018

OTHER PUBLICATIONS

International Search Report dated Jun. 26, 2019 in PCT/KR2019/003220 filed on Mar. 20, 2019, 4 pages.
Kim et al., "miR-150 enhances apoptotic and anti-tumor effects of paclitaxel in paclitaxel-resistant ovarian cancer cells by targeting Notch3", Oncotarget,, 2017, vol. 8, No. 42, pp. 72788-72800 (14 total pages).
Shao et al., "Involvement of non-coding RNAs in chemotherapy resistance of ovarian cancer", Journal of Cancer, 2018, vol. 9, No. 11, pp. 1966-1972 (8 total pages).
Jeong et al., "MicroRNA-136 inhibits cancer stem cell activity and enhances the anti-tumor effect of paclitaxel against chemoresistant ovarian cancer cells by targeting Notch3", Cancer Letters, 2017, vol. 386, pp. 168-178 (12 total pages).
Prahm et al., "Clinical validation of chemotherapy predictors developed on global microRNA expression in the NCI60 cell line panel tested in ovarian cancer", PLoS One, 2017, vol. 12, No. 3, e0174300, pp. 1-15.
Kim et al., "Differential microRNA expression signatures and cell type-specific association with Taxol resistance in ovarian cancer cells", Drug Design, Development and Therapy, 2014, vol. 8, pp. 293-314.
Cui et al., "MicroRNAs: key players of taxane resistance and their therapeutic potential in human cancers", Journal of Cellular and Molecular Medicine, 2013, vol. 17, No. 10, 14 total pages.
Lin et al., "MicroRNAs as potential therapeutics to enhance chemosensitivity in advanced prostate cancer", Scientific Reports, 2018, vol. 8, 16 total pages.
The Journal of Urology, e1326, 2017, vol. 197, No. 4S, Supplement, 1 page.

* cited by examiner

*Primary Examiner* — Sean McGarry
(74) *Attorney, Agent, or Firm* — Oblon, McClelland, Maier & Neustadt, L.L.P.

(57) ABSTRACT

According to a composition, kit, and method for diagnosing resistance to a taxane anticancer agent, a composition for treating taxane cancer agent-resistant cancers, and a method for screening materials for the same, taxane anticancer agent-resistant cancers may be efficiently diagnosed or treated, and candidate materials that may treat taxane anticancer agent-resistant cancers may be efficiently screened.

6 Claims, 33 Drawing Sheets
Specification includes a Sequence Listing.

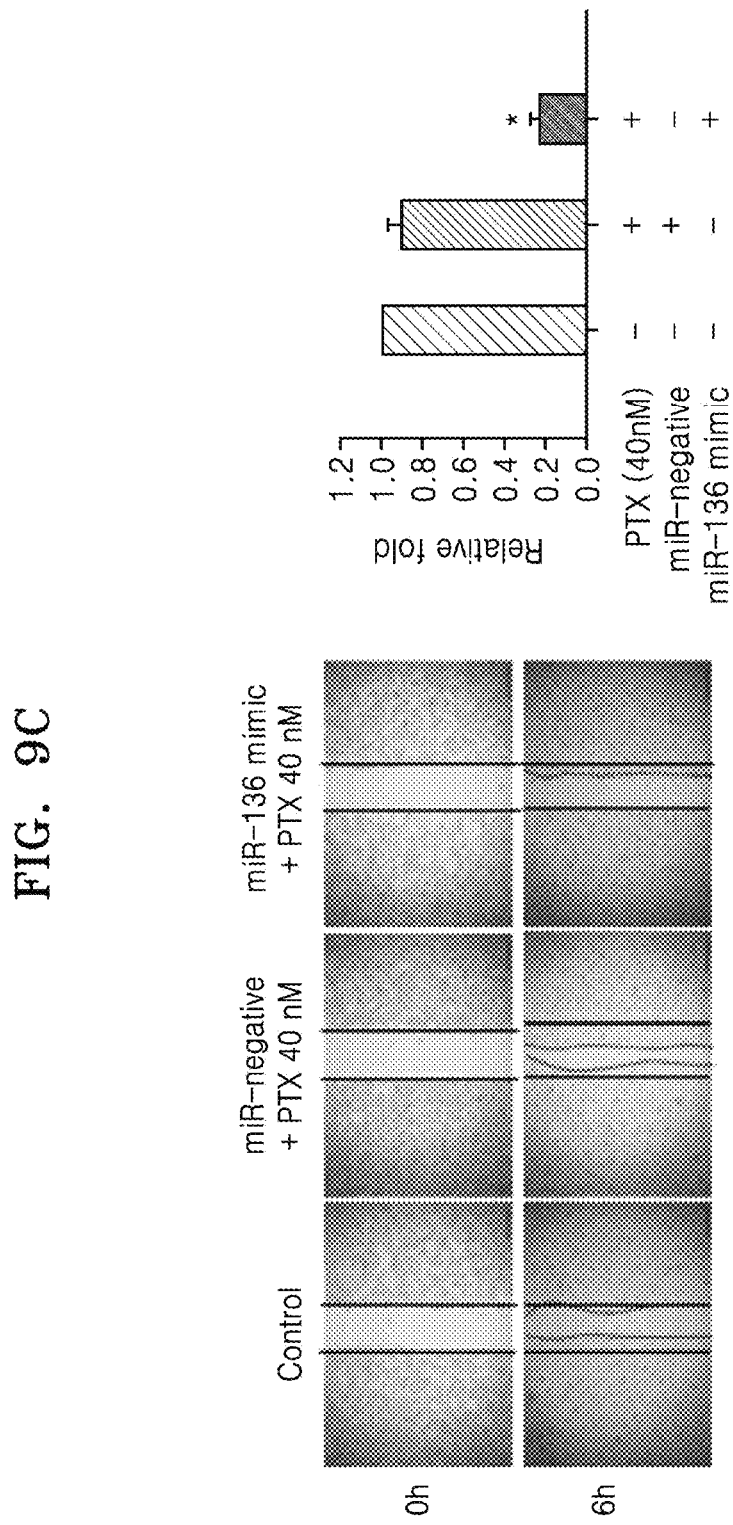

SEQUENCE LISTING

<160> NUMBER OF SEQ ID NOS: 2

<210> SEQ ID NO 1
<211> LENGTH: 22
<212> TYPE: RNA
<213> ORGANISM: Artificial sequence
<220> FEATURE:
<223> OTHER INFORMATION: miR-150

<400> SEQUENCE: 1
cugguacagg ccuggggac ag                                     22

<210> SEQ ID NO 2
<211> LENGTH: 84
<212> TYPE: RNA
<213> ORGANISM: Artificial sequence
<220> FEATURE:
<223> OTHER INFORMATION: pre miR-150

<400> SEQUENCE: 2
cuccccaugg cccugucucc caacccuugu accagugcug ggcucagacc cugguacagg     60 ccuggggac agggaccugg ggac                                            84

COMPOSITION, KIT, AND METHOD FOR DIAGNOSIS AND TREATMENT OF TAXANE ANTICANCER AGENT-RESISTANT CANCER

SEQUENCE LISTING

The instant application contains a Sequence Listing which has been submitted electronically in ASCII format and is hereby incorporated by reference in its entirety. Said ASCII copy, created on Jun. 4, 2021, is named 534549USSL.txt and is 839 bytes in size.

TECHNICAL FIELD

The present disclosure relates to a composition, a kit, and a method for diagnosis and treatment of a taxane anticancer agent-resistant cancer.

BACKGROUND ART

Ovarian carcinoma is a cancer that has the highest lethality among female malignancies. This high lethality results from chemoresistance and frequent recurrence of ovarian carcinoma. Several agents have been developed to prevent or treat ovarian carcinoma, but the mortality and rate of recurrence of ovarian carcinoma are still high.

Recently, interest in cancer stem cells (CSCs), which exist in small numbers within tumors and have high tumorigenic capacity, has been increasing. CSCs were initially isolated from ovarian serous carcinomas (OSCs) by a spheroid formation assay, and are presumed to be one of the major causes of recurrence and chemoresistance in cancers (Korean Patent No. 10-2017-0063198). However, no effective strategies for reducing ovarian CSCs and lowering the high recurrence and mortality rates of ovarian cancer have been developed yet.

DESCRIPTION OF EMBODIMENTS

Technical Problem

Provided is a composition for diagnosing resistance to a taxane anticancer agent, the composition including an agent for measuring an expression level of microRNA-150 (miR-150).

Provided is a kit for diagnosing resistance to a taxane anticancer agent, the kit including an agent for measuring an expression level of miR-150.

Provided is a method of providing information for diagnosis of resistance to a taxane anticancer agent or a method of diagnosing resistance to a taxane anticancer agent, the methods including measuring an expression level of miR-150 from a sample of an individual.

Provided is a pharmaceutical composition for treating a taxane anticancer agent-resistant cancer, the composition including miR-150 as an active ingredient.

Provided is a method of screening a taxane anticancer agent-resistant cancer treating agent, the method including measuring an expression level of miR-150 from a sample of an individual, to which a candidate material for treatment of a taxane anticancer agent-resistant cancer is administered.

Solution to Problem

According to an aspect of the present disclosure, provided is a composition for diagnosis of resistance to a taxane anticancer agent, the composition including an agent for measuring an expression level of microRNA-150 (miR-150); and a use of the agent for diagnosis of resistance to a taxane anticancer agent.

As used herein, the term "miR, miRNA, or microRNA" denotes a non-coding short RNA which functions as a post-transcriptional regulator during gene expression. These RNAs complementarily bind to target mRNAs having a complementary nucleotide sequence and thus degrade the target mRNAs or inhibit translation of the target mRNAs into proteins. In particular, miRNA is transcribed into precursors of about 70 nucleotides (nts) to about 80 nts in length having a hairpin structure called pre miRNA, cleaved with a dicer, an RNAse III enzyme, and then produced in a matured form. The miRNAs form a ribonucleotide complex called miRNP, which binds complementarily to the target site to cleave the target gene or inhibit translation. Over 30% of human miRNAs are present with clusters, but they are transcribed into a single precursor and then cleaved to finally form matured miRNA. As used herein, the term "miRNA" may be used as meaning an intermediate form of an RNA transcript, that is, pri-miRNA (primary transcript) or pre miRNA (precursor). The "miR-150" is one of the miRNA precursor families found in mammals including humans and is known to be closely related to the toxicity of natural killer cells and the functionality of intestinal immune cells.

As used herein, the term "diagnosis" refers to confirming the presence or characteristics of a pathological condition and may include confirming the presence or absence of taxane anticancer agent-resistance or the onset or possibility of occurrence of a taxane anticancer agent-resistant cancer.

As used herein, the term "anticancer agent-resistance" refers that when a cancer patient is treated with an anticancer agent, the agent has no cancer-treating effect from the beginning of the treatment or has cancer-treating effect at the beginning but loses the cancer-treating effect in the course of continuous treatment. In the treatment using anticancer agents, the general treatment effect assessment is classified into four categories according to the criteria established by the world health organization (WHO): (1) tumor completely disappears and persist without tumor for at least 4 weeks (complete response); (2) 50% or more reduction in tumor size (partial response); (3) less than 50% reduction in tumor size (stable disease); and (4) 25% or more increase in tumor size (progressive disease). That is, based on the WHO criteria, when a cancer patient is treated with an anticancer agent, the anticancer agent-resistance refers to having no cancer-treating effect from the beginning of the treatment [(1) and (2)] or having cancer-treating effect at the beginning but losing the cancer-treating effect in the course of continuous treatment [(3) and (4)]. Here, the anticancer agent may be a taxane-based anticancer drug or may be, for example, one selected from paclitaxel, docetaxel, larotaxel, cabazitaxel, and a combination thereof.

The "measuring of an expression level" may be found by ascertaining a miRNA gene itself or a miRNA level in which the gene is expressed, that is, an expression level of protein coded with the miRNA gene. For example, an expression level of miR-150 may be measured using an antisense oligonucleotide, a primer pair, or a probe that specifically binds to the miR-150.

The "antisense oligonucleotide" may refer to an oligomer having a sequence of nucleotide bases and a subunit-to-subunit backbone that allows the antisense oligomer to hybridize to a target sequence in RNA by Watson-Crick base paring, to form a miRNA and an RNA: oligomer heteroduplex within the target sequence. The oligomer may have exact sequence complementarity to the target sequence, or near complementarity thereto.

The "primer" means a nucleic acid sequence strand having a free 3' hydroxyl group, which is able to form a base pair with a template complementary to a specific base sequence, and functions as a starting point for amplifying the template. The primer may initiate DNA synthesis in the presence of a regent for polymerization in a suitable buffer solution at a suitable temperature (DNA polymerase or reverse transcriptase) and four different nucleoside triphosphates. For example, polymerase chain reaction (PCR) amplification may be performed using sense and antisense primers having 7 to 50 nucleotide sequences as primers specific to miR-150 to measure an amount of a desired product, thereby diagnosing resistance to a taxane anticancer agent in an individual. PCR conditions and length of sense and antisense primers may be modified on the bases of the methods known in the art. The primer may have 10 to 100 nts, 15 to 100 nts, 10 to 80 nts, 10 to 50 nts, 10 to 30 nts, 10 to 20 nts, 15 to 80 nts, 15 to 50 nts, 15 to 30 nts, 15 to 20 nts, 20 to 100 nts, 20 to 80 nts, 20 to 50 nts, or 20 to 30 nts.

The term "probe" may refer to a fragment of nucleic acid such as an RNA or DNA that is ones to hundreds of base pairs capable of specifically binding to miRNA and which may be labeled to identify the presence, amount, and expression level of specific miRNA. A probe may be prepared in a form of oligonucleotide probe, single stranded DNA probe, double stranded DNA probe, or RNA probe. For example, the resistance to a taxane anticancer agent in an individual may be diagnosed by performing hybridization using a probe having a nucleic acid sequence complementary to miR-150 and measuring an expression level from a degree of the hybridization. Modification may be made of probe selection and hybridization condition, based on methods known in the art. The probe may have 10 to 100 nts, 15 to 100 nts, 10 to 80 nts, 10 to 50 nts, 10 to 30 nts, 10 to 20 nts, 15 to 80 nts, 15 to 50 nts, 15 to 30 nts, 15 to 20 nts, 20 to 100 nts, 20 to 80 nts, 20 to 50 nts, or 20 to 30 nts.

Also, the antisense oligonucleotide, primer, or probe may be chemically synthesized according to a phosphoramidite solid support method or other synthesis methods known in the art. The nucleotide sequence may be modified using various methods known in the art. Examples of such modifications may include methylation, capping, substitution with one or more homologues of natural nucleotide, and modification between nucleotides, for example, modification into an uncharged linker (e.g., methyl phosphonate, phosphotriester, phosphoroamidate, or carbamate) or charged linker (e.g., phosphorothioate or phosphorodithioate). In addition, the primer or probe may be modified using an indicator capable of directly and/or indirectly providing a detectable signal. Examples of the indicator may include a radioactive isotope, a fluorescent molecule, and biotin.

In one embodiment, it is found that reduced expression of miR-150 in tumor cell or tissue is associated with taxane anticancer agent-resistance. Thus, an expression level of miR-150 may be used in diagnosis of taxane anticancer agent-resistance.

Also, the composition may further include an agent for measuring an expression level of one selected from the group consisting of miR-136, miR-23b, miR-27b, miR-326, miR-424, miR-503, and a combination thereof. Here, taxane anticancer agent-resistance may be diagnosed from expression reduction of miR-136; or expression increase of miR-23b, miR-27b, miR-326, miR-424, and/or miR-503.

The sequences of miR-150, miR-136, miR-23b, miR-27b, miR-326, miR-424, and miR-503 may be evaluated in publicly available databases such as www.microRNA.org, www.mirbase.org, or www.mirz.unibas.ch/cgi/miRNA.cgi. miRNAs are generally numbered according to a naming convention such as "mir-[number]". The number of a miRNA is assigned according to its order of discovery relative to previously identified miRNA species. When a miRNA is discovered as homologous to a known miRNA from a different organism, the name may be given an optional organism identifier, of the form [organism identifier]-mir-[number]. Mature microRNA is commonly designated with the prefix "miR" whereas the gene or precursor miRNA is designated with the prefix "mir". As used herein, any microRNA (miRNA or miR) designated with prefix mir-* or miR-* is understood to encompass both the precursor and/or mature species, unless explicitly stated otherwise. Further details of miR naming may be found at www.mirbase.org or Ambros et al., A uniform system for microRNA annotation, RNA 9:277-279 (2003).

According to another embodiment, provided is a kit for diagnosis of resistance to a taxane anticancer agent, the kit including an agent for measuring an expression level of miR-150.

The kit may have an effect of diagnosing resistance to a taxane anticancer agent by measuring an expression level of miR-150. The kit may further include one or more types of other component compositions, solutions, or devices, as well as antisense oligonucleotides, primer pairs, or probes for diagnosing taxane anticancer agent-resistance. Examples of the kit may include a RT-PCR kit, a microarray chip kit, and a DNA chip kit.

The kit for measuring an expression level of miR-150 may be a kit including elements necessary to perform RT-PCR. The RT-PCR kit may include, in addition to primer pairs each specific for maker genes, a test tube or other proper containers; reaction buffer solutions; deoxynucleotides (dNTPs); enzymes, such as a Taq-polymerase and a reverse transcriptase; DNase and RNase inhibitors, DEPC-water; or sterilized water.

In addition, the kit for measuring an expression level of miR-150 may be a kit including essential elements necessary to perform a microarray. The microarray kit may include a substrate where a gene or cDNA, which is a fragment of the gene, is attached as a probe, and the substrate may include a gene of a quantitative control group or cDNA, which is a fragment of the gene. The microarray kit may be prepared using a marker according to a manufacturing method commonly used in the art. In order to prepare the microarray, a micropipetting method using a piezoelectric manner in order to fix a DNA chip on the substrate using the searched marker as DNA molecule, or a method using a spotter in the shape of pin may be used. The substrate of the microarray chip may be a chip coated with an active group selected from the group consisting of amino-silane, poly-L-lysine, and aldehyde. Also, the substrate of the microarray chip may be selected from the group consisting of slide glass, plastic, metal, silicon, nylon membrane, and nitrocellulose membrane.

The kit for measuring an expression level of miR-150 may be a kit including essential elements necessary to perform a DNA chip. The DNA chip kit may include a substrate where a gene or cDNA, which is a fragment of the gene, or oligonucleotide is attached, a reagent, a formulation, and an enzyme for preparing fluorescent probes. Also, the substrate may include a control group gene or cDNA, which is a fragment of the gene, or oligonucleotide.

Also, the kit may further include an agent for measuring an expression level of one selected from the group consisting of miR-136, miR-23b, miR-27b, miR-326, miR-424, miR-503, and a combination thereof.

Among the terms or elements mentioned above in relation to the kit, those mentioned in the description of the composition are understood as the same with those mentioned above in the description of the composition.

According to another embodiment, provided is a method of providing information for diagnosis of resistance to a taxane anticancer agent or a method of diagnosing resistance to a taxane anticancer agent, the methods including (a) measuring an expression level of miR-150 from a sample of an individual; and (b) comparing the measured expression level of miR-150 with an expression level of a normal control sample.

As used herein, the term "individual" denotes an individual that is being subject to confirmation or prediction of the presence or absence of taxane anticancer agent-resistant therein. The individual may be a vertebrate, for example, a mammal, an amphibian, a reptile, or a bird, or, for example, may be a mammal, for example, a human (*Homo sapiens*).

As used herein, the term "sample" may include whole blood, serum, plasma, saliva, urine, sputum, lymph, cell, or tissue, or, for example, may be tumor cell or tumor tissue.

The term "a method of measuring an expression level" may refer to at least one selected from the group consisting of reverse transcription polymerase chain reaction (RT-PCR), competitive RT-PCR, real-time RT-PCR, RNase protection assay, Northern blotting, and DNA chip.

In this method, when the expression level of miR-150 from the sample of an individual is decreased relative to an expression level of a normal control group, the sample may be determined as resistant to a taxane anticancer agent. Such a change in the expression level in the individual may refer to an expression level of the sample similar with that of a normal control group or a positive control group; or an expression level decreased by at least 1%, 2%, 3%, 4%, 5%, 10%, 20%, 30%, 40%, 50%, 60%, 70%, 80%, 90%, or 100% as compared with that of a normal control group or a positive control group.

Also, the method may further include measuring an expression level of one selected from the group consisting of miR-136, miR-23b, miR-27b, miR-326, miR-424, miR-503, and a combination thereof from a sample of an individual, and comparing the expression level with an expression level of a normal control sample. Here, when the expression level of miR-136 measured from a sample of an individual is decreased relative to an expression level of a normal control group, the sample may be determined as resistant to a taxane anticancer agent, and when the expression level of miR-23b, miR-27b, miR-326, miR-424, and/or miR-503 measured from a sample of an individual is increased relative to an expression level of a normal control group, the sample may be determined as resistant to a taxane anticancer agent.

Among the terms or elements mentioned above in relation to the method of providing information for diagnosis, those mentioned in the description of the composition or kit are understood as the same with those mentioned above in the description of the composition or kit.

According to another embodiment, provided is a pharmaceutical composition for treating a taxane anticancer agent-resistant cancer, the composition including miR-150 as an active ingredient; a use of the composition for treating a taxane anticancer agent-resistant cancer; and a method of treating a taxane anticancer agent-resistant cancer, the method including administering the composition to an individual.

As used herein, the term "treatment" refers to all actions involved in alleviating or beneficially changing symptoms of taxane anticancer agent-resistant cancer by administration of the pharmaceutical composition according to an embodiment.

The "cancer," which is a disease to be treated by the composition according to an embodiment, encompasses diseases caused by cells having an aggressive characteristic such that cells are divided and grown by ignoring a normal growth limit, an invasive characteristic such that cells are infiltrated into peripheral tissue, and a metastatic characteristic such that cells are spread to other parts of the body.

According to the onset site of cancer, the cancer may be one selected from the group consisting of ovarian cancer, liver cancer, colon cancer, cervical cancer, kidney cancer, stomach cancer, prostate cancer, breast cancer, brain tumor, lung cancer, uterine cancer, colorectal cancer, bladder cancer, and pancreatic cancer, and may be taxane anticancer agent-resistant cancer in the therapeutic point of view of cancer.

The pharmaceutical composition may be carried in pharmaceutically acceptable carriers, such as colloidal suspensions, powders, saline, lipids, liposomes, microspheres, or nano spherical particles. These may form or be related to a complex with a vehicle and may be carried or delivered in vivo by using carrying systems known in the art, such as lipids, liposomes, microparticles, gold, nanoparticles, polymers, condensation reagents, polysaccharides, polyamino acids, dendrimers, saponin, adsorption enhancing substances, or fatty acids.

In one embodiment, the pharmaceutical composition may be used for gene therapy. Particularly, the gene therapy refers to a technique of treating diseases by gene transfer and regulation of gene expression, wherein effective cancer treatment effect may be obtained by regulating expression of target miRNA and genes related to the target miRNA. In this regard, miR-150 may be included in a viral or non-viral vector and may be delivered or transported in vivo. Examples of the viral vector may include adenovirus, vaccinia virus, lentivirus, retrovirus, and herpes simplex virus, and examples of the non-viral vector may include plasmid vector, bacteriophage vector, liposome, bacterial artificial chromosome, and yeast artificial chromosome. In addition, miR-150 may be mixed with a biocompatible polymer or enclosed in a biocompatible polymer to be delivered or transported in vivo.

Examples of the pharmaceutically acceptable carriers in general preparation may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, magnesium stearate, and mineral oil, but embodiments are not limited thereto. The pharmaceutical composition may further include, in addition to the above ingredients, a lubricant, a wetting agent, a sweetener, a flavoring agent, an emulsifier, a suspending agent, and a preservative.

The pharmaceutical composition may be administered orally or parenterally (for example, intramuscularly, intravenously, intraperitoneally, subcutaneously, intradermally, or topically) depending on the intended method, and the dose may vary according to the condition and weight of a patient, the degree of disease, a type of drug, and the route and time of administration, but may be suitably selected by those skilled in the art.

The pharmaceutical composition is administered with a pharmaceutically effective dose. As used herein, the term "pharmaceutically effective dose" refers to an amount which is sufficient to treat the diseases at a reasonable benefit/risk ratio applicable to medical treatment, and an effective dose level may be determined according to elements including a kind of disease of the patient, the severity, activity of a drug, sensitivity to a drug, a time of administration, a route of administration, and an emission rate, duration of treatment, and simultaneously used drugs and other elements known in the medical field. The pharmaceutical composition may be administered as an individual therapeutic agent or in combination with other anticancer agents, simultaneously, separately, or sequentially administered with existing anticancer agents, and administered singly or multiply. In particular, according to an embodiment, since the composition may significantly improve sensitivity of tumor cells to a taxane anticancer agent, the composition may improve anticancer effect by being used in combination with a taxane anticancer agent.

The effective dose of the pharmaceutical composition may vary according to age, gender, condition, and weight of the patient, absorption of active ingredients in the body, inactive rate, excretion rate, disease type, and combined drugs, and may be increased or decreased according to the route of administration, the severity of obesity, gender, weight, and age.

Also, the pharmaceutical composition may further include miR-136 or may include an agent that inhibits an expression level of one selected from the group consisting of miR-23b, miR-27b, miR-326, miR-424, miR-503, and a combination thereof.

Among the terms or elements mentioned above in relation to the pharmaceutical composition for treating a taxane anticancer agent-resistant cancer, those mentioned in the description of the composition, kit, or method for diagnosis are understood as the same with those mentioned above in the description of the composition, kit, or method for diagnosis.

According to another embodiment, provided is a method of screening a therapeutic agent of a taxane anticancer agent-resistant cancer, the method including (a) measuring an expression level of miR-150 from a sample of an individual to which a candidate material for treating a taxane anticancer agent-resistant cancer is administered; and (b) comparing the measured expression level of miR-150 with an expression level of a normal control sample.

As used herein, the term "candidate material" refers to a newly synthesized or known compound, which may include any material that is expected to have an effect on treating a taxane anticancer agent-resistant cancer.

The "administration" of the candidate drug denotes introduction of a material to an individual in an appropriate manner. The route of administration of the candidate material may be any general route, as long as the candidate material may reach a target tissue. The candidate material may be administered intraperitoneally, intravenously, intramuscularly, subcutaneously, intradermally, orally, topically, intranasally, intrapulmonarily, or intrarectally.

When the expression level of miR-150 measured from a sample of an individual is increased relative to that of a normal control group, the method may include determining the composition as a therapeutic agent of a taxane anticancer agent-resistant cancer. The increase of the expression level may refer to an expression level of the sample similar with a normal control group or a negative control group; or an expression level increased by at least 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900%, and 1000% as compared with that of a normal control group or a negative control group.

Also, the method may further include measuring an expression level of one selected from the group consisting of miR-136, miR-23b, miR-27b, miR-326, miR-424, miR-503, and a combination thereof from a sample of an individual to which a candidate material for treating a taxane anticancer agent-resistant cancer is administered, and comparing the expression level with an expression level of a normal control sample. Here, when the expression level of miR-136 measured from a sample of an individual is increased relative to an expression level of a normal control group, the candidate composition may be determined as a therapeutic agent of a taxane anticancer agent-resistant cancer, and when the expression level of miR-23b, miR-27b, miR-326, miR-424, and/or miR-503 measured from a sample of an individual is decreased relative to an expression level of a normal control group, the candidate composition may be determined as a therapeutic agent of a taxane anticancer agent-resistant cancer.

Among the terms or elements mentioned above in relation to the screening method, those mentioned in the description of the composition, kit, or method for diagnosis are understood as the same with those mentioned above in the description of the composition, kit, or method for diagnosis.

Advantageous Effects of Disclosure

As described above, a composition according to one or more embodiments not only may be efficiently used in diagnosis of resistance to a taxane anticancer agent but also may contribute in treating a taxane anticancer agent-resistant cancer and screening a therapeutic agent related to a taxane anticancer agent-resistant cancer. Therefore, the composition is expected to be applied as a core technology in the field of diagnosis and treatment of taxane anticancer agent-resistant cancer.

Figure 3:
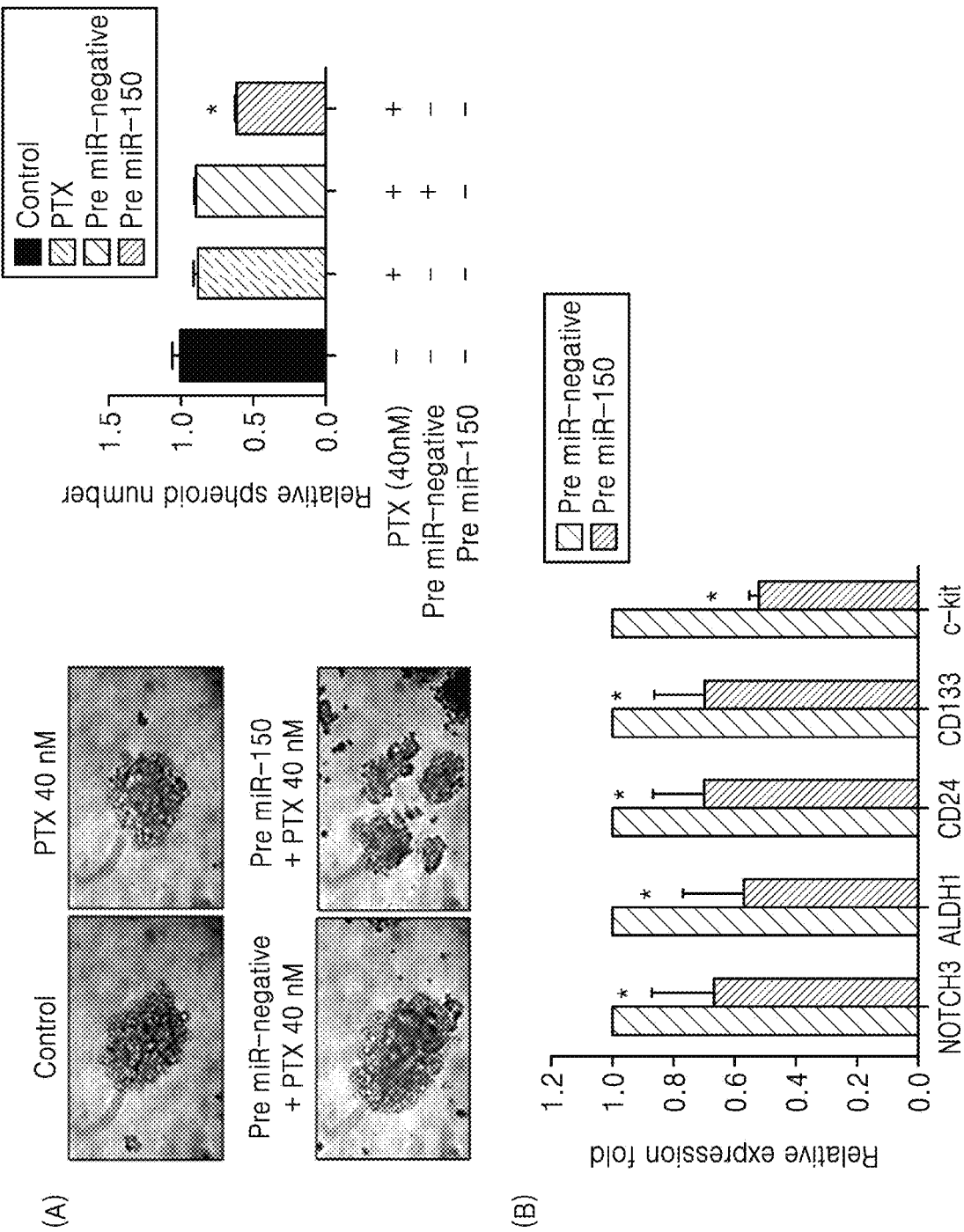
Figure 4A:
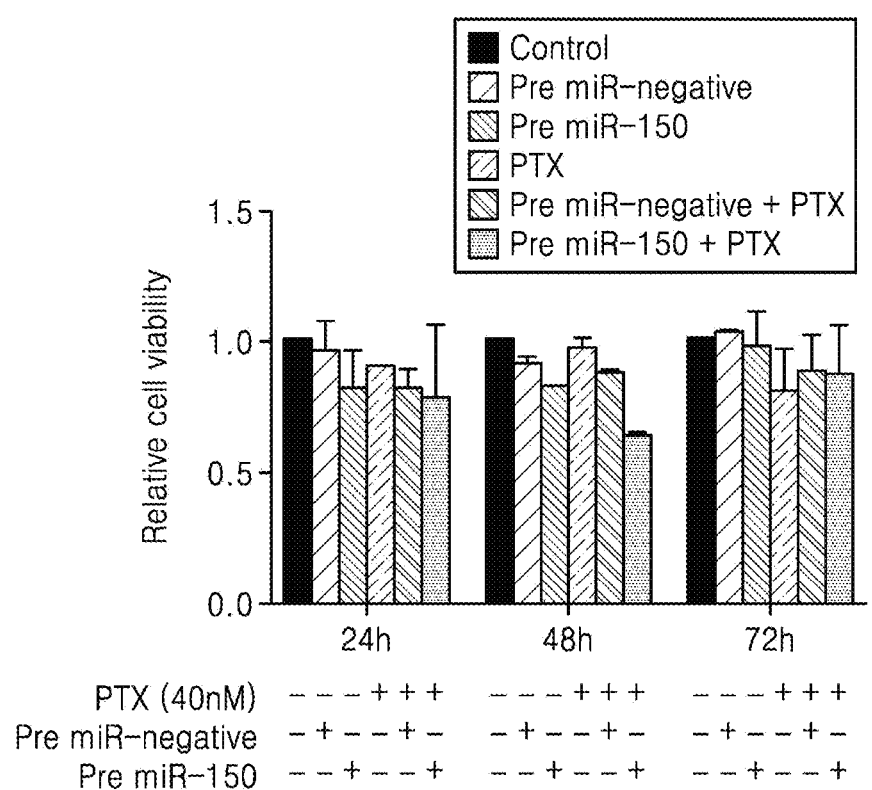
Figure 4B:
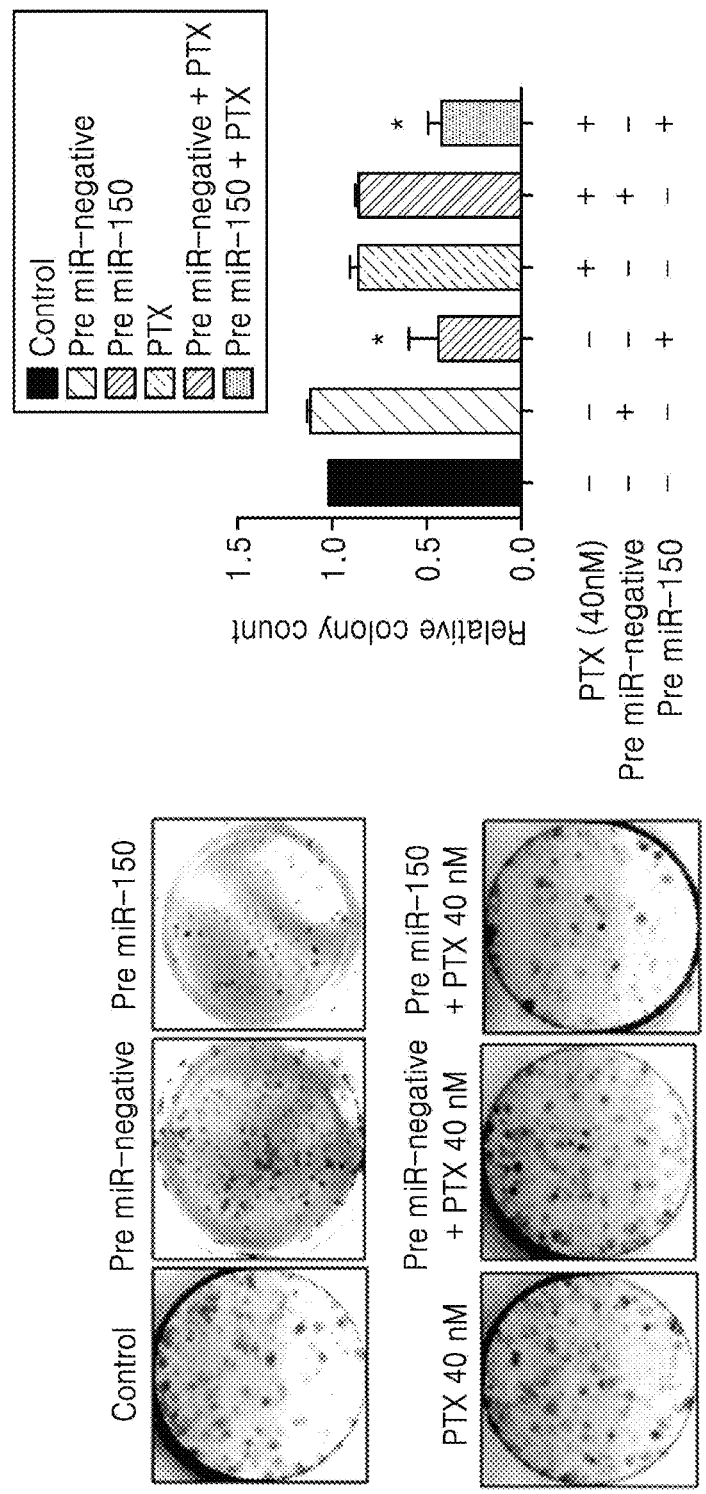
Figure 4C:
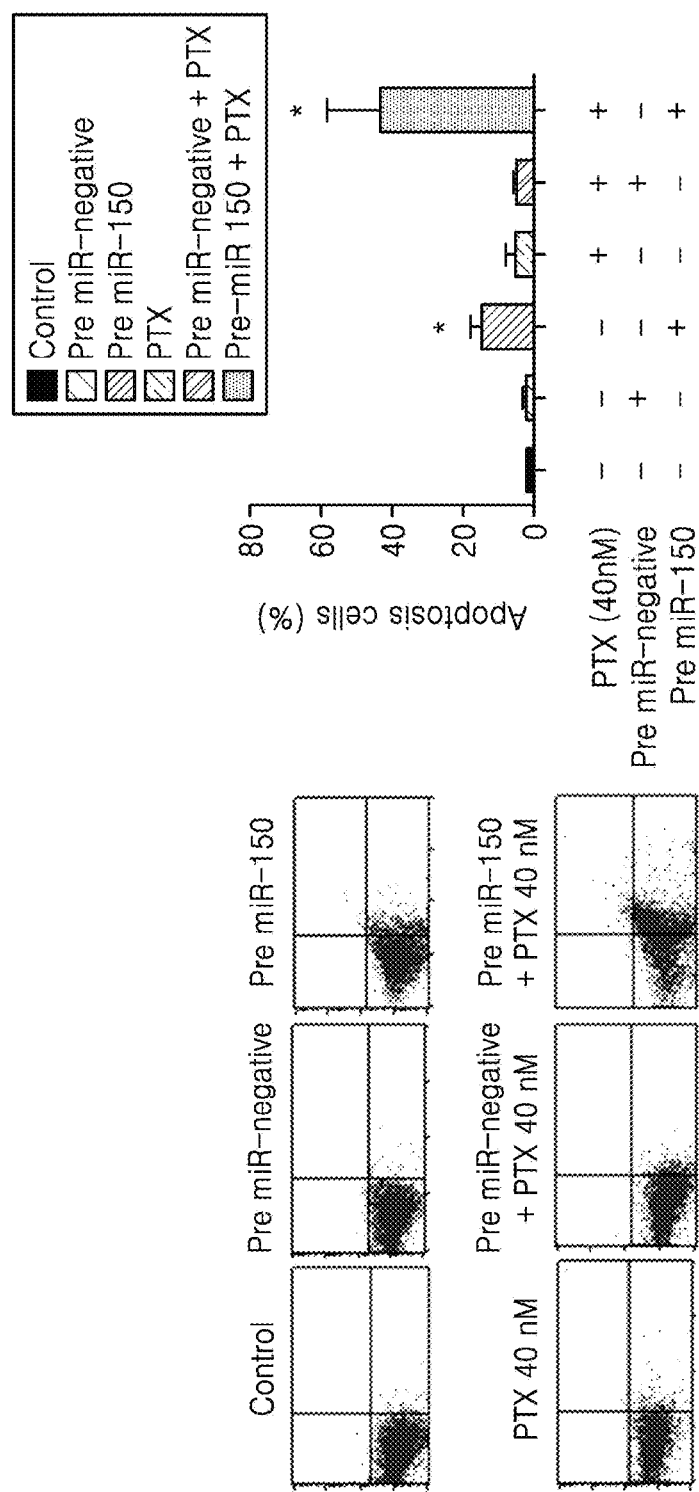
Figure 5A:
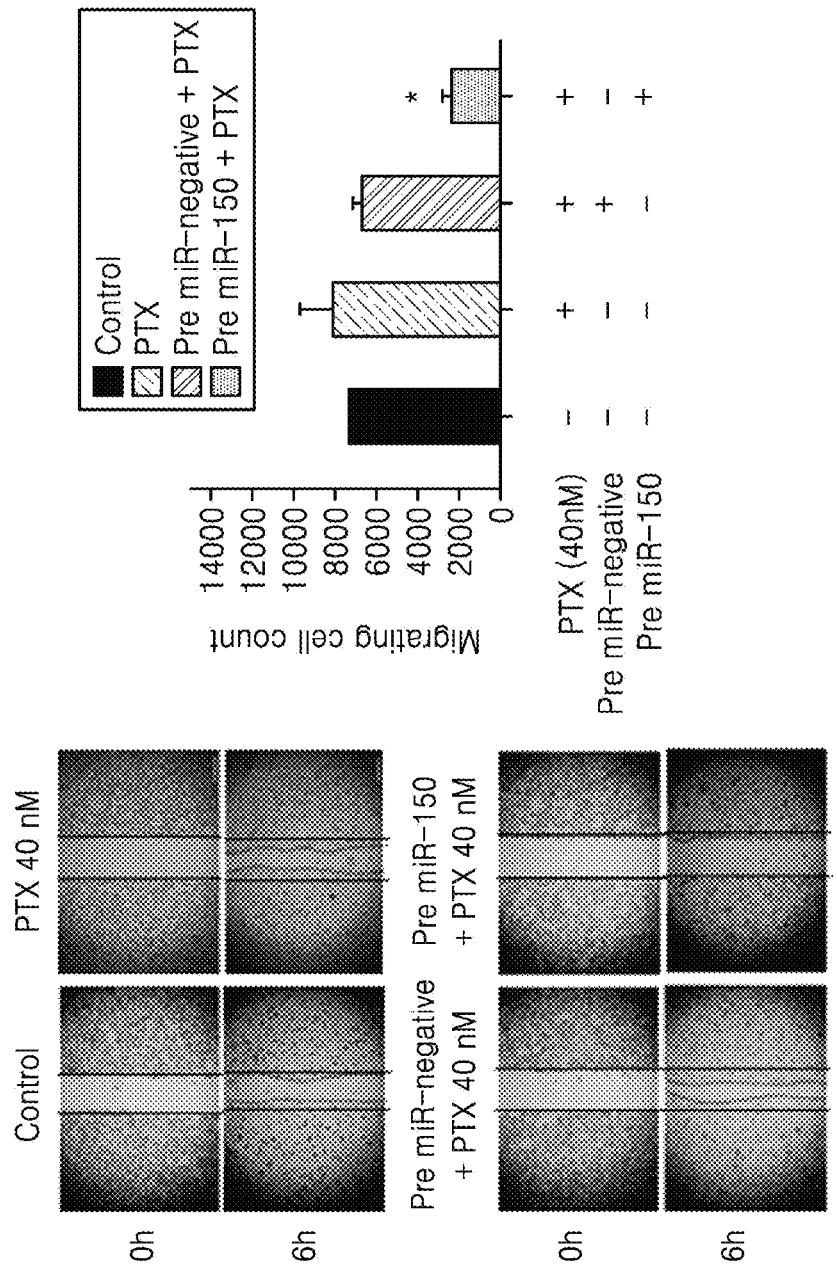
Figure 5B:
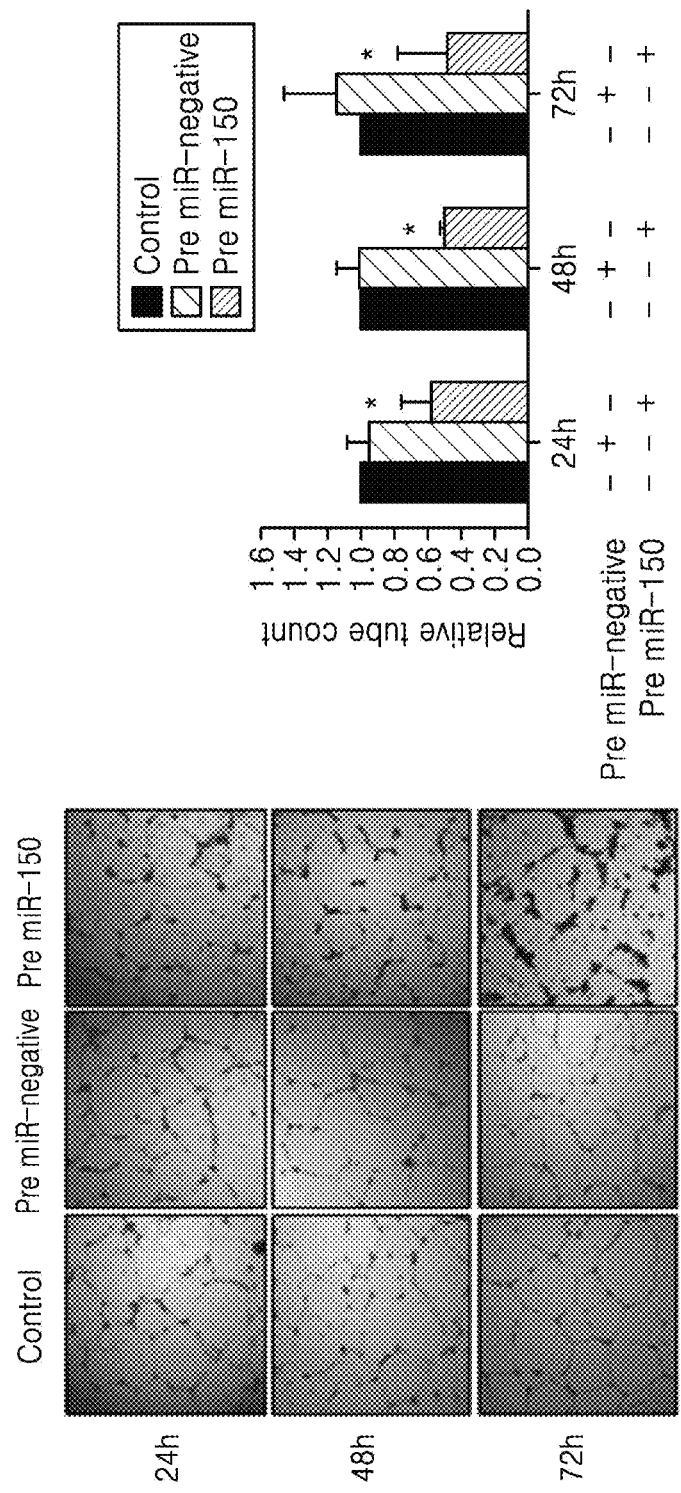
Figure 6A:
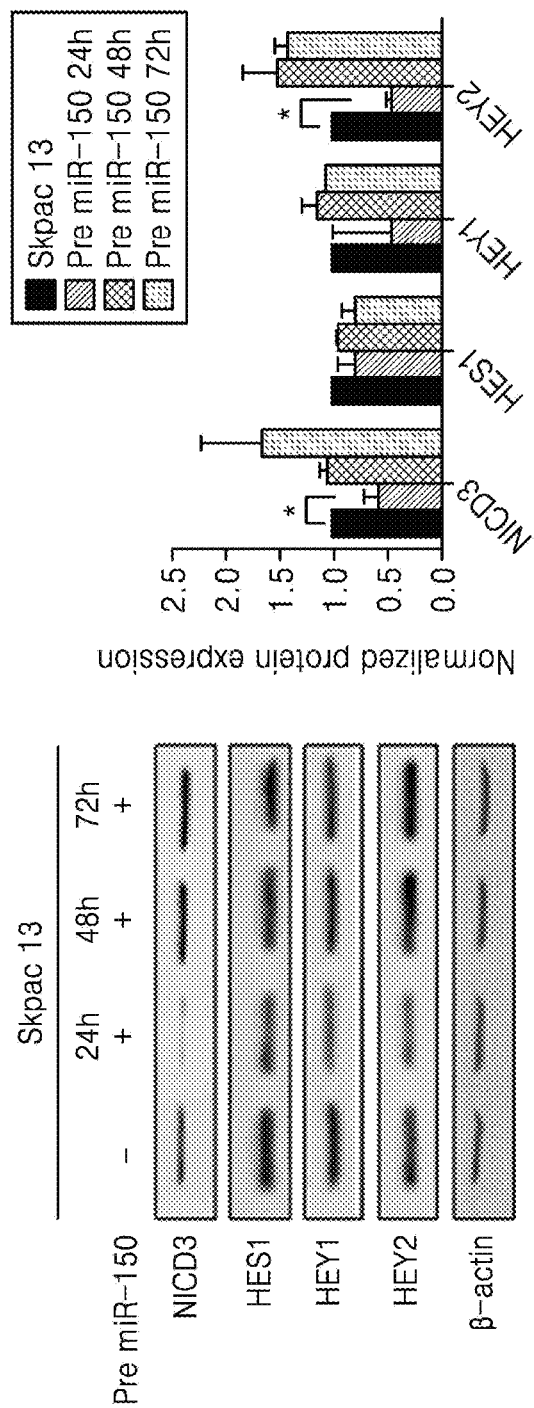
Figure 6B:
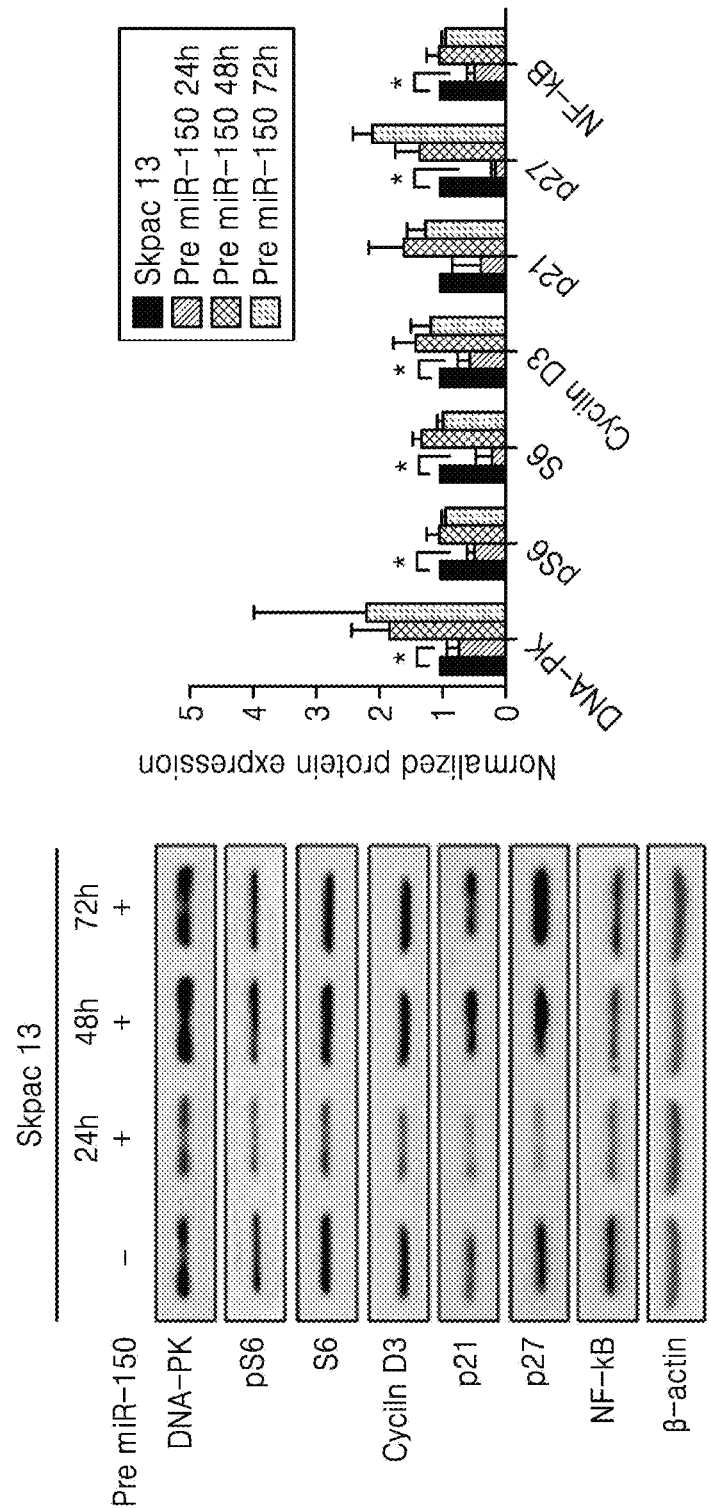
Figure 6C:
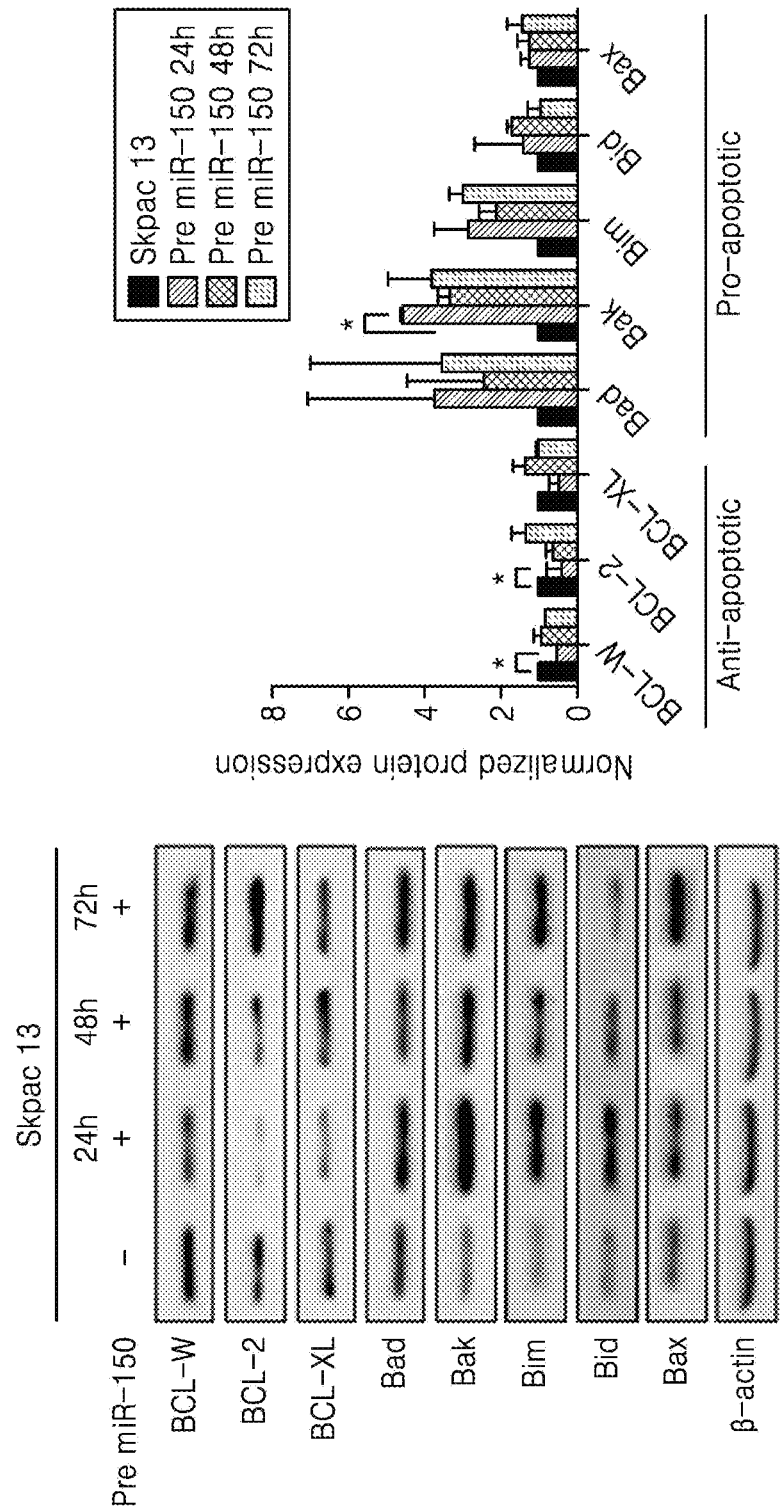
Figure 7A:
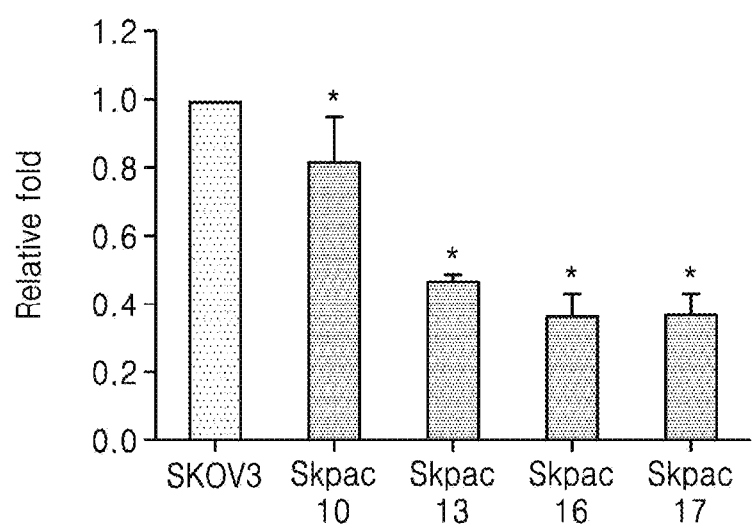
Figure 7B:
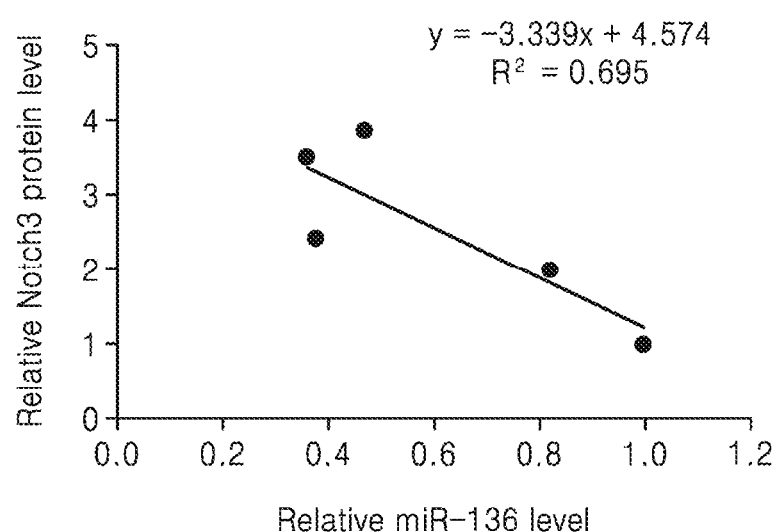
Figure 7C:
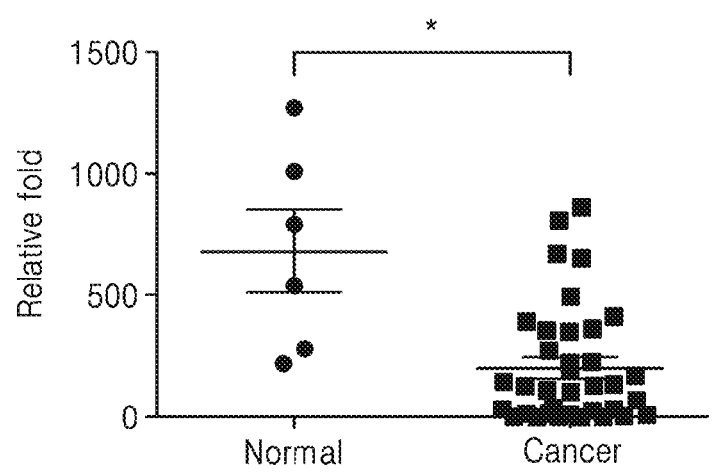
Figure 7D:
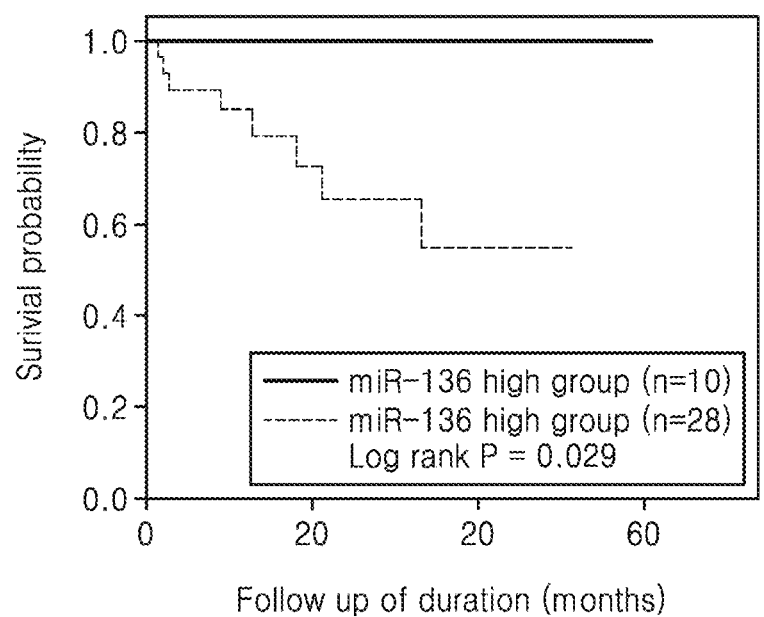
Figure 7E:
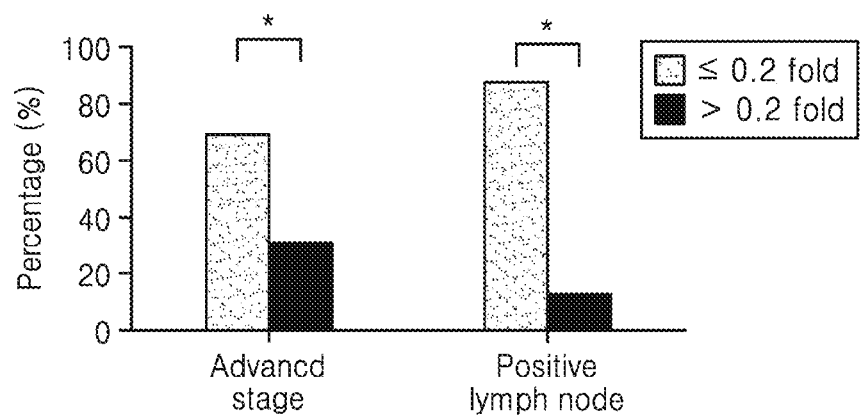
Figure 8A:
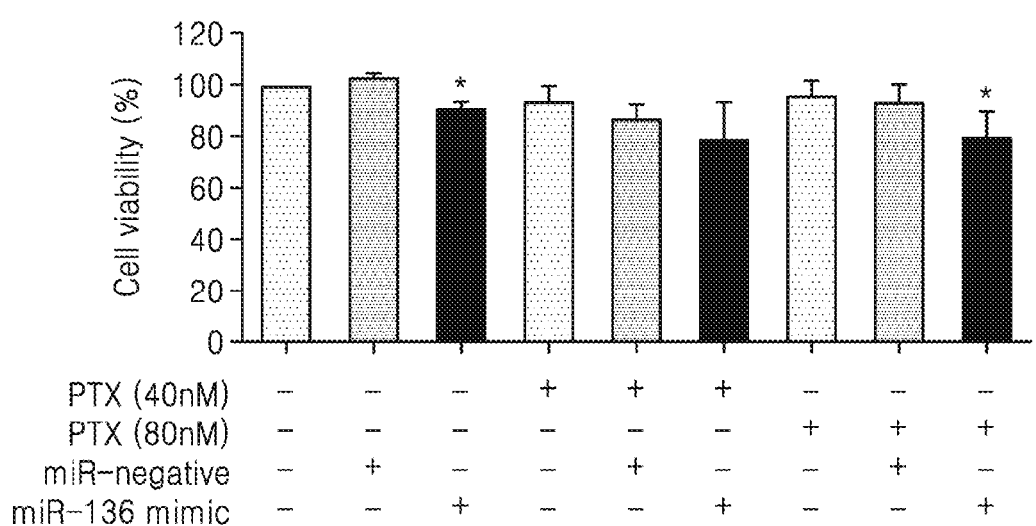
Figure 8B:
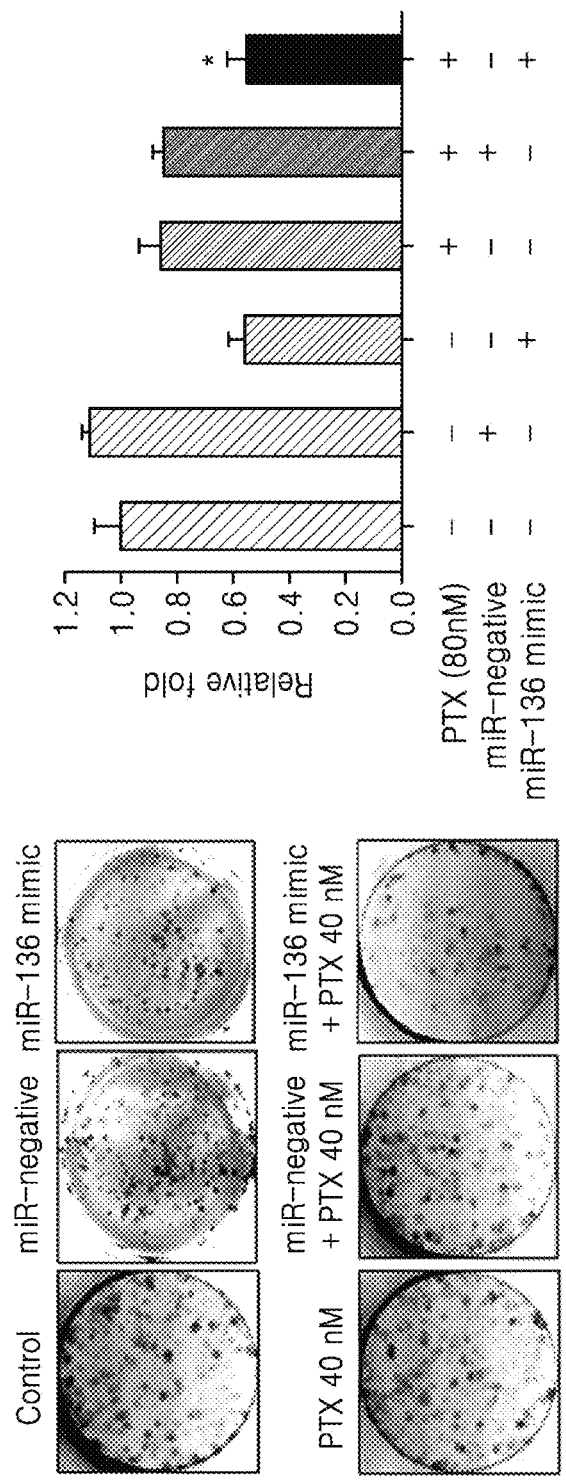
Figure 8C:
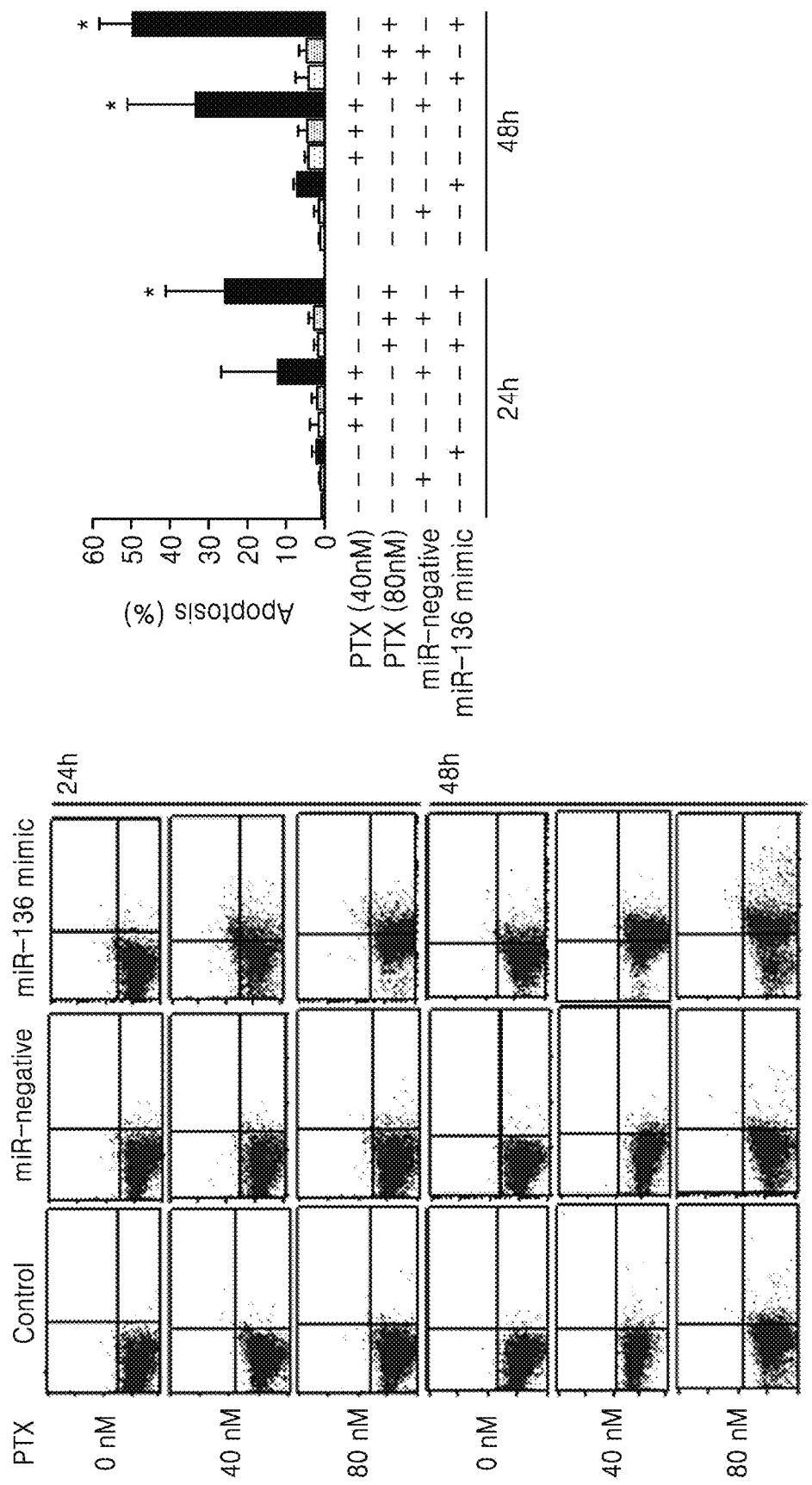
Figure 9A:
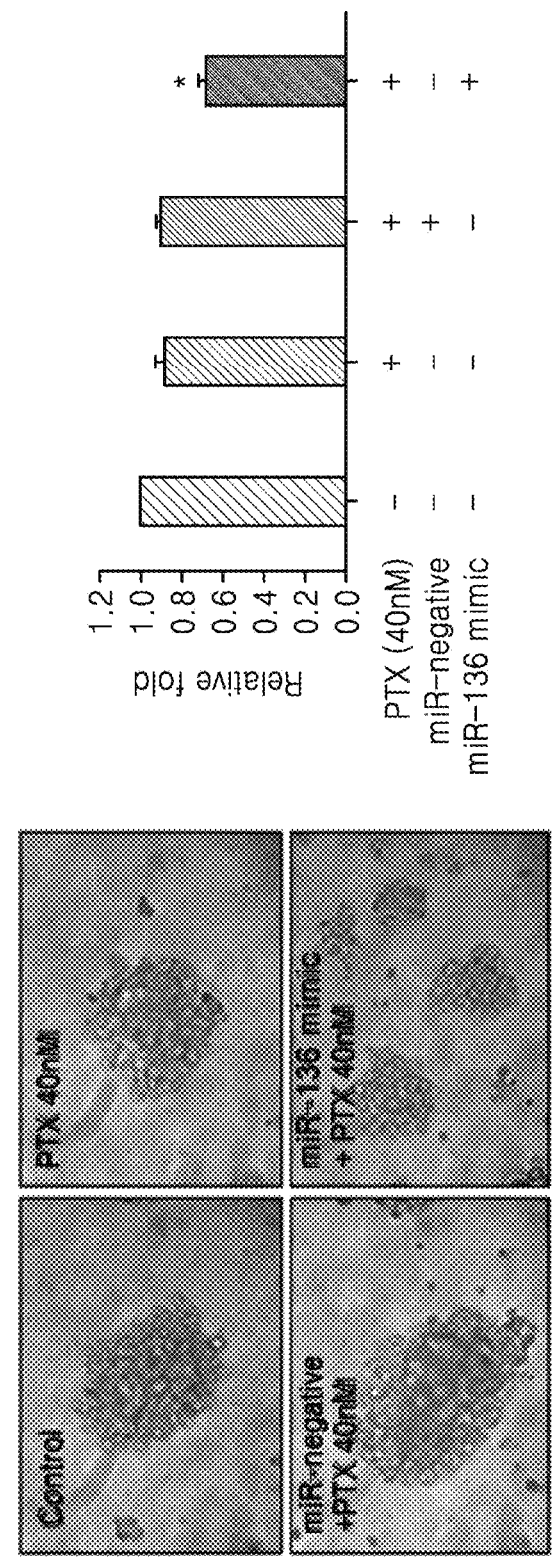
Figure 9B:
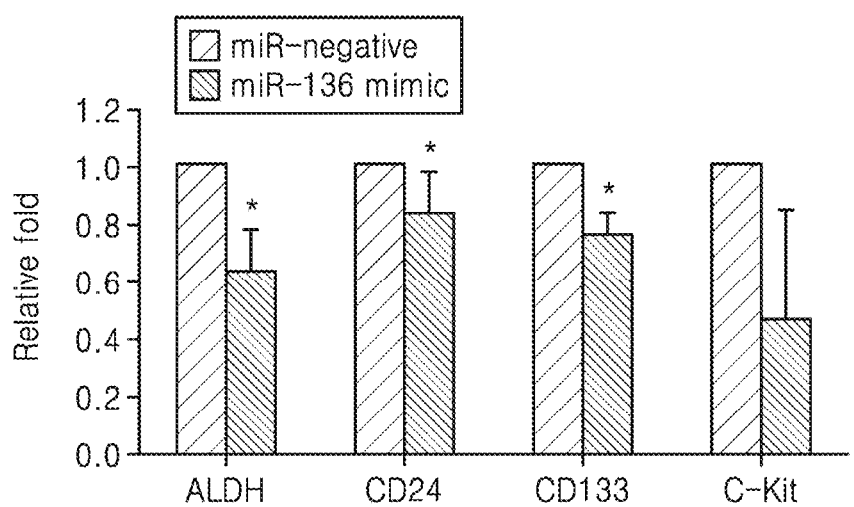
Figure 9D:
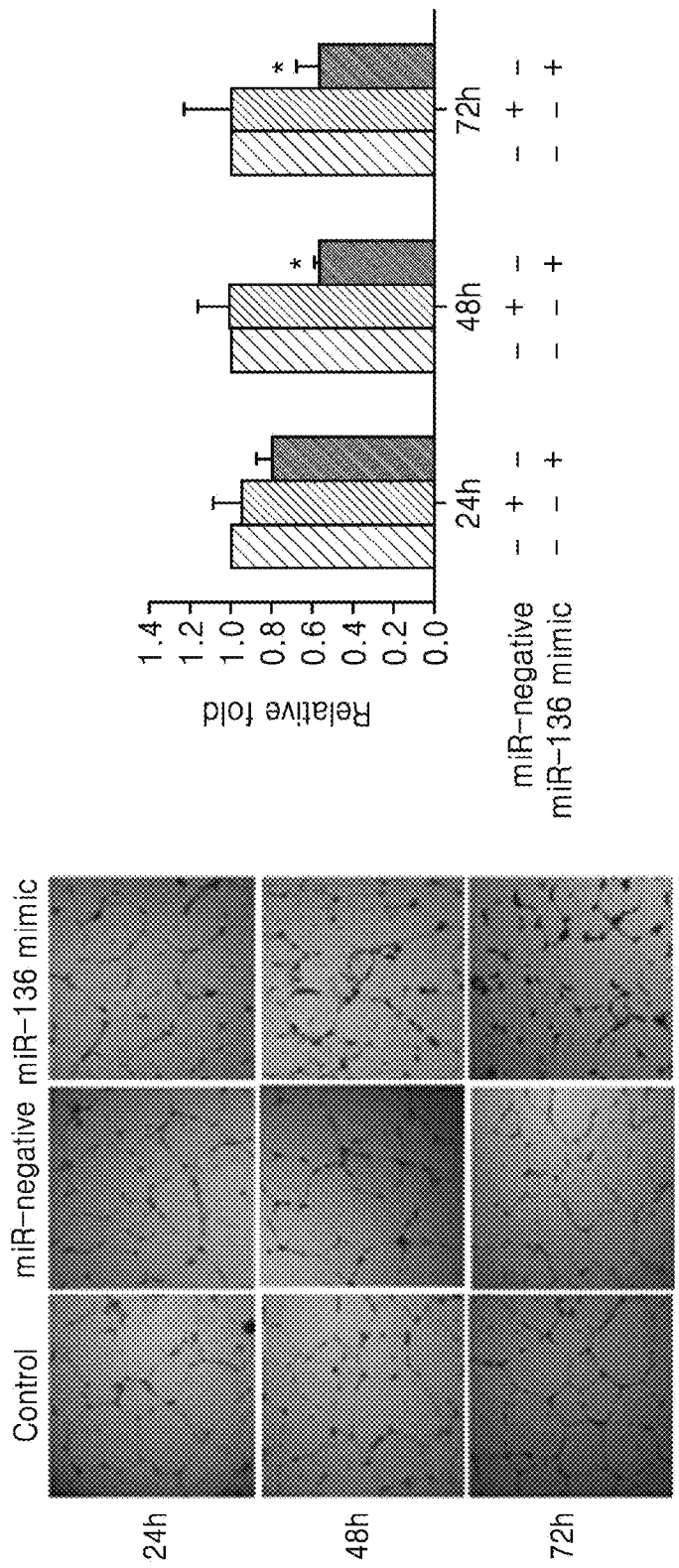
Figure 10A:
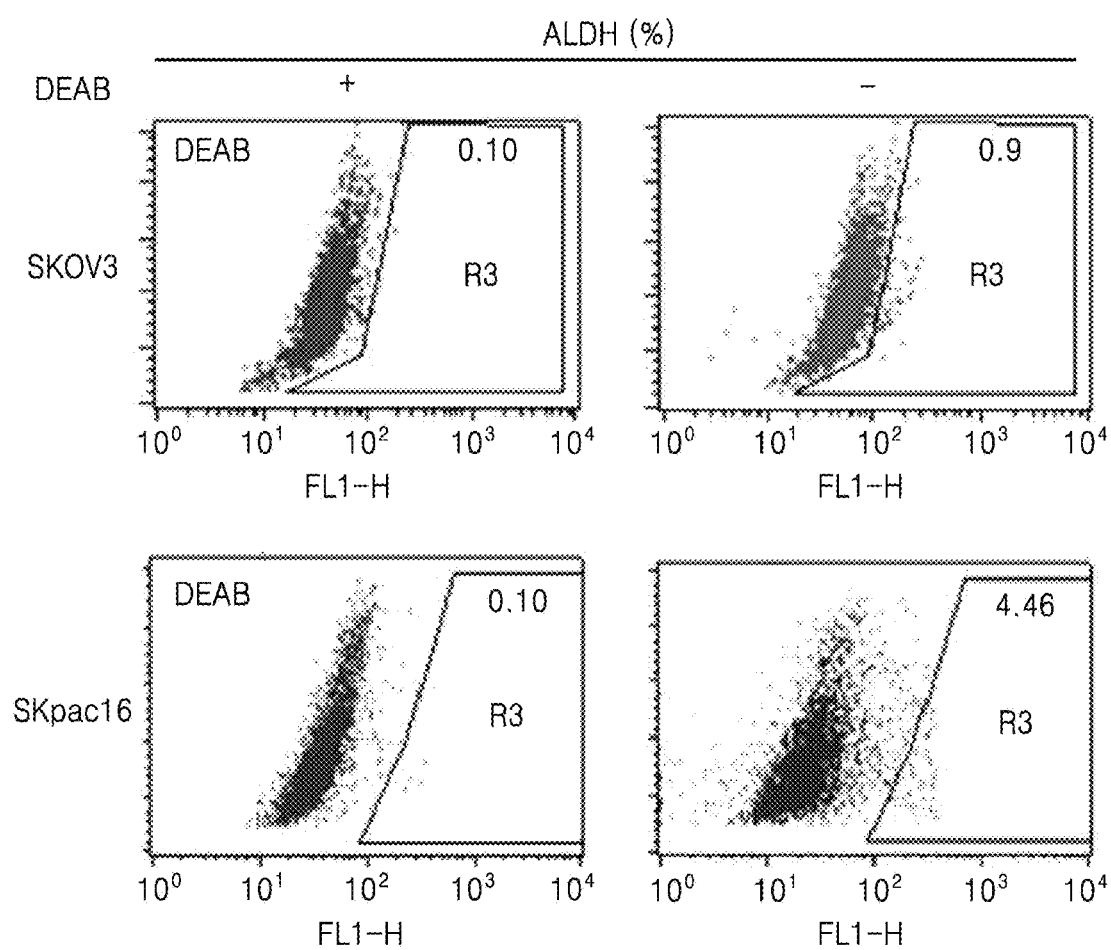
Figure 10B:
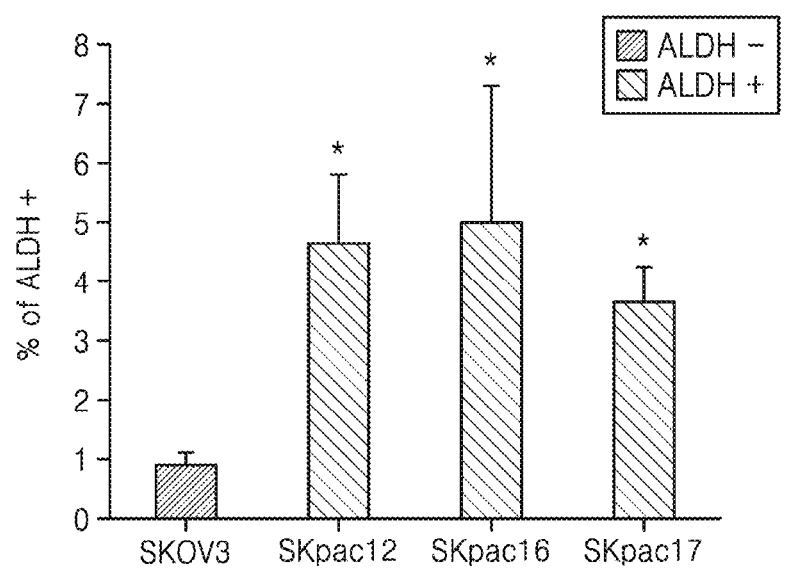
Figure 10C:
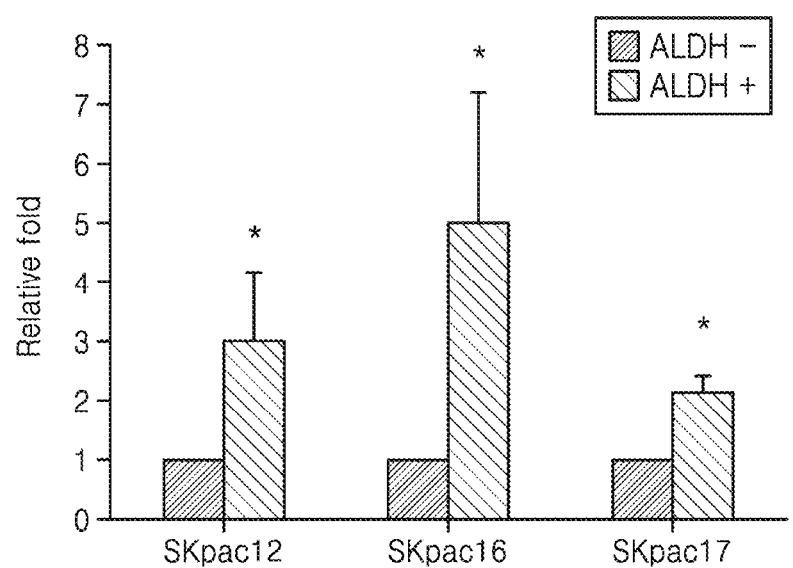
Figure 11:
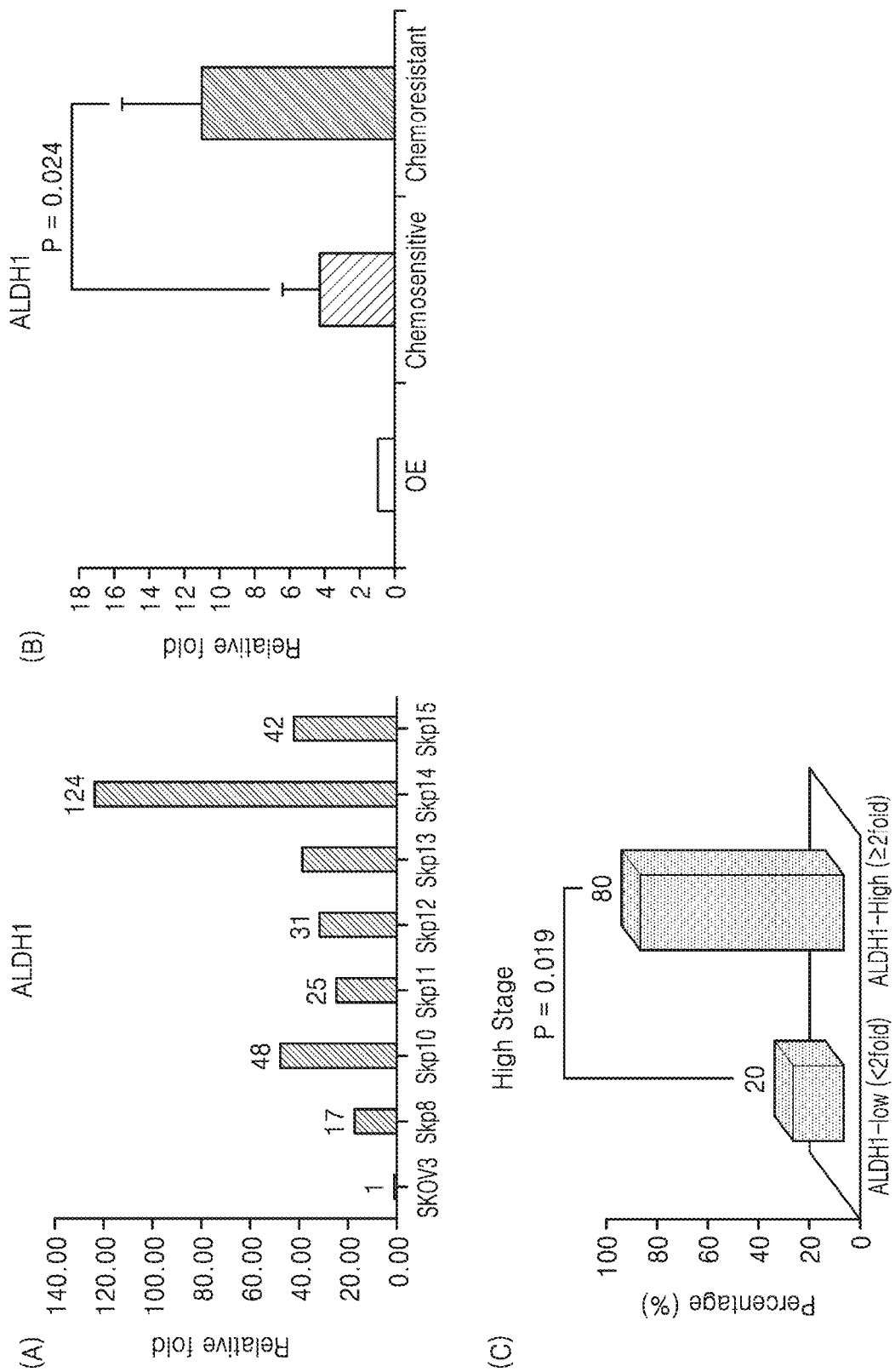
Figure 12A:
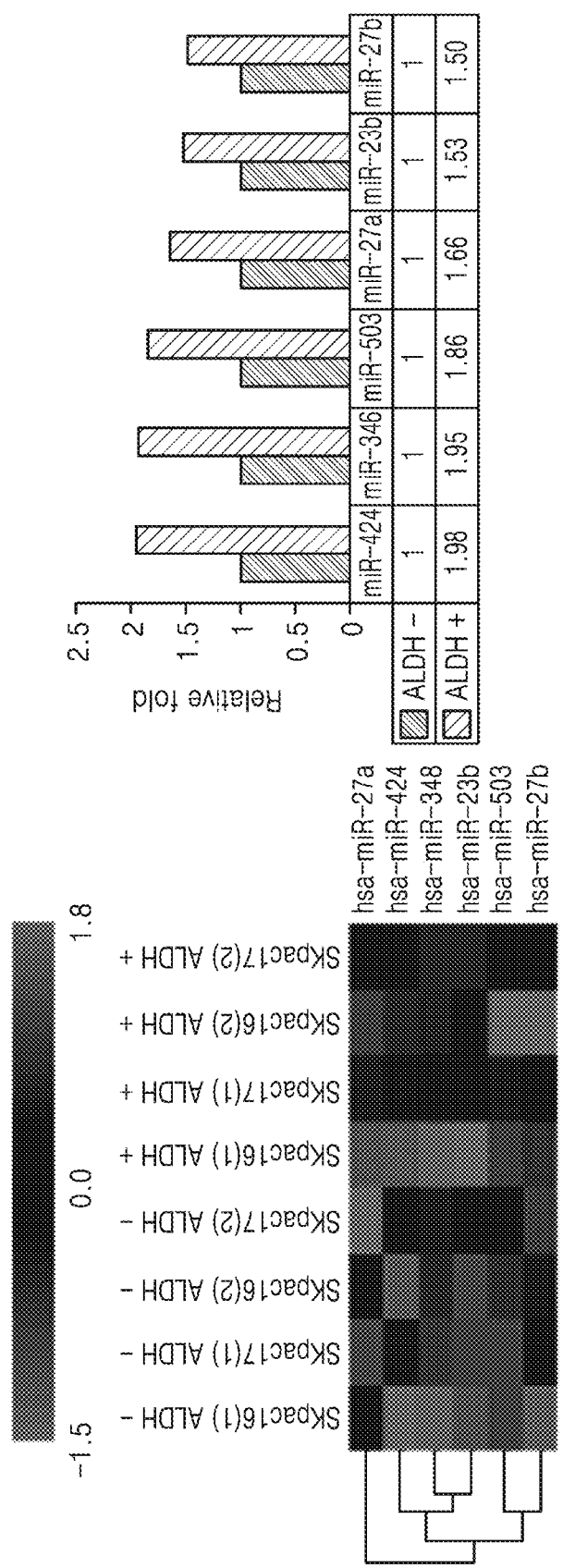
Figure 12B:
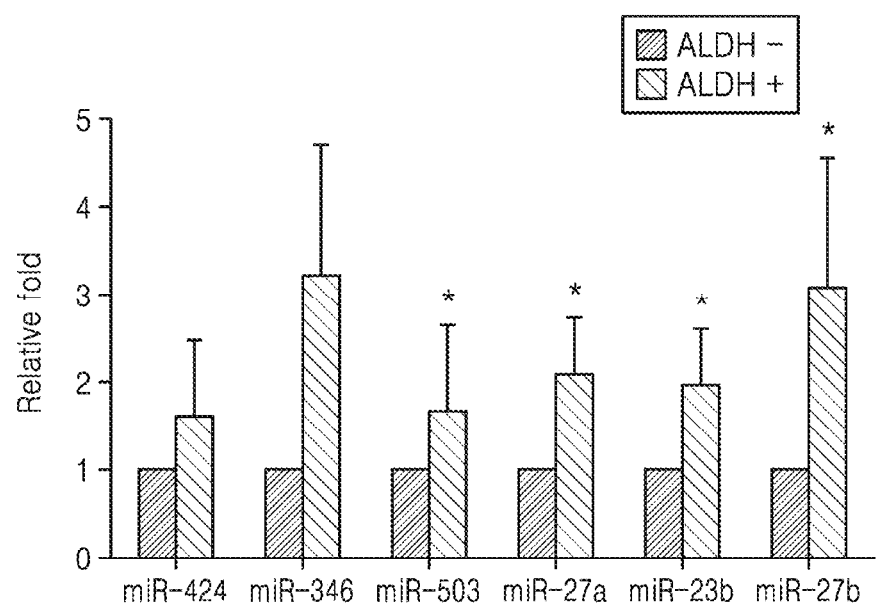
Figure 13A:
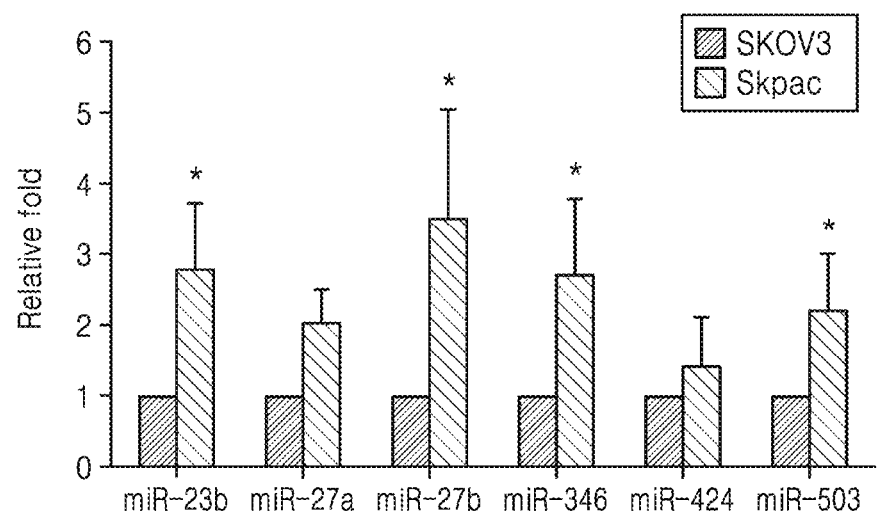
Figure 13B:
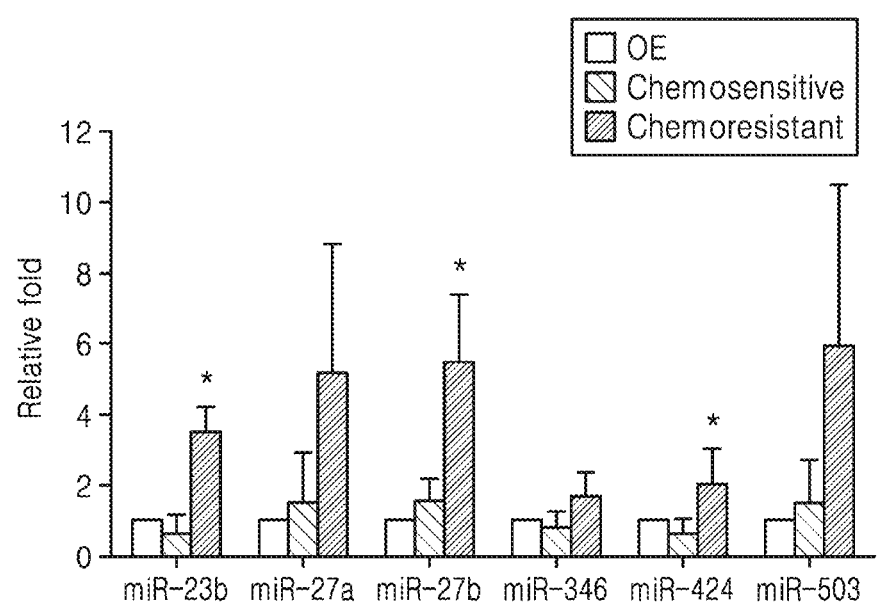
Figure 13C:
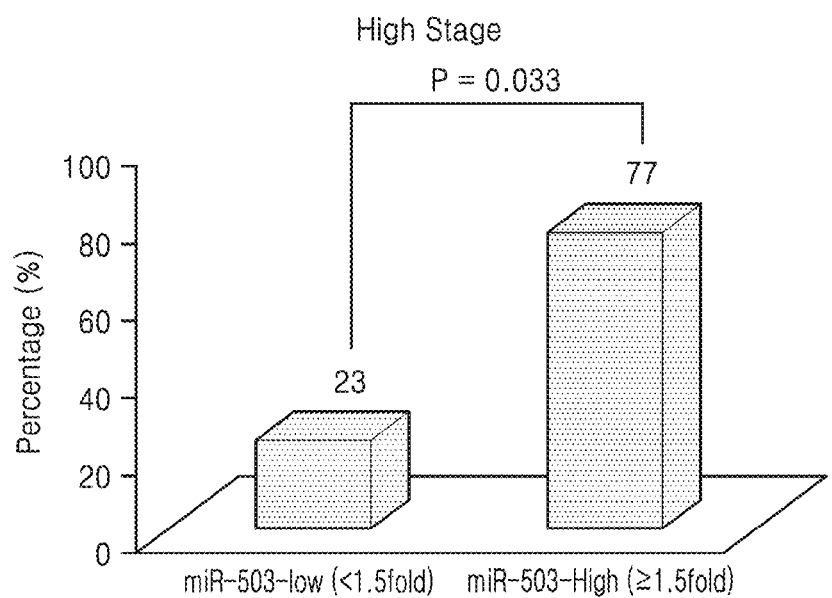
Figure 13D:
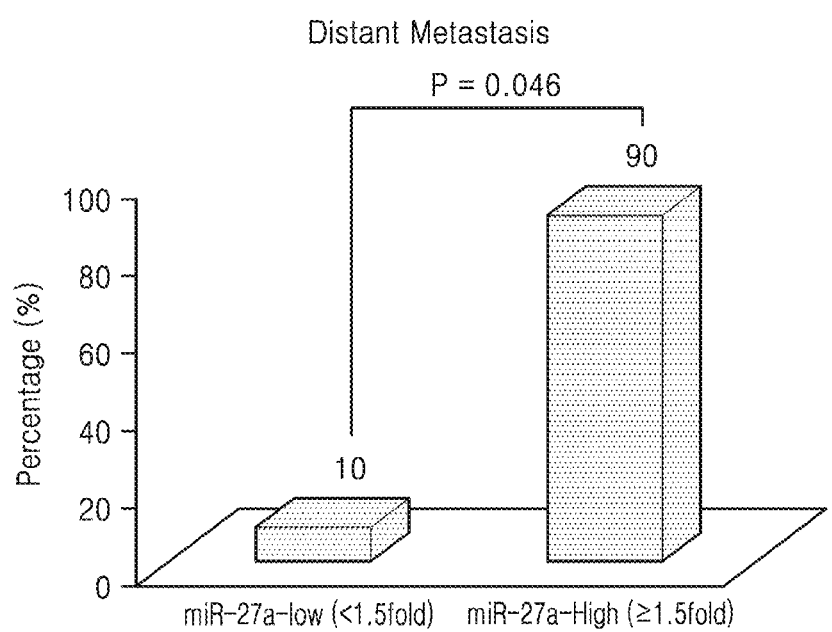

FIG. 3 shows results of confirming effects of miR-150 transfection with respect to activity of cancer stem cells (CSCs) using a spheroid formation assay, wherein A of FIG. 3 shows results of the spheroid formation assay, wherein it was confirmed that the number and size of spheroids significantly decreased in SKpac-17 cells transfected with PTX and pre miR-150 as compared with that of a control group, a group treated with PTX (40 nM) alone, and a group treated with pre miR-negative siRNA+PTX (*P<0.05), and B of FIG. 3 shows results of measuring mRNA expression of key stem cell markers after treating PTX-resistant SKpac cells (SKpac-12, SKpac-13, and SKpac-17 cells) with pre miR-150, wherein average mRNA expression levels of NOTCH3, ALDH1, CD24, CD133, and c-Kit significantly decreased respectively by about 0.67-fold, 0.57-fold, 0.70-fold, 0.70-fold, and 0.51-fold as compared with the control group (*P<0.05);

FIGS. 4A to 4C show results of confirming effects of pre miR-150 with respect to cell viability, cell proliferation, and apoptosis of SKpac cells, FIG. 4A shows results of a WST assay, wherein the cell viability of the group treated with PTX and pre miR-150 decreased by about 34% as compared with a group treated with PTX alone in SKpac cells at 48 hours, FIG. 4B shows results of a colony formation assay, wherein SKpac cell proliferation of a group treated with pre miR-150 alone and the group treated with PTX and pre miR-150 respectively decreased by about 44% and 43% as compared with the group treated with PTX alone or the group treated with pre miR-negative+PTX (*P<0.05), and FIG. 4C shows results of a TUNEL assay, wherein SKpac cell apoptoses of the group treated with pre miR-150 alone and the group treated with PTX and pre miR-150 respectively increased by about 14.4% and 40.6% as compared with the group treated with PTX alone or the group treated with pre miR-negative+PTX (*P<0.05);

FIGS. 5A and 5B show results of confirming effects of pre miR-150 with respect to migration and angiogenesis of SKpac cells, FIG. 5A shows results of a wound healing assay, wherein cell migration of the group treated with pre miR-150 (40 nM) decreased by about 28.7% and 36% as compared with the group treated with PTX alone and the group treated with pre miR-negative+PTX, respectively, (*P<0.05), and FIG. 5B shows results of a tube formation assay, wherein the cells transfected with pre miR-150 showed tube formation reduced by about 61.1% at 24 hours, about 50.5% at 48 hours, and 42.6% at 72 hours as compared with a control group of HUVECs using pre miR-negative cells (*P<0.05);

FIGS. 6A to 6C show results of confirming expression of protein in SKpac cells after pre miR-150 transfection, wherein FIG. 6A confirms expression of Notch downstream molecules after pre miR-150 transfection, FIG. 6B confirms expression of protein associated with cell survival and cell cycle after pre miR-150 transfection, and FIG. 6C confirms expression of protein associated with apoptosis after pre miR-150 transfection;

FIGS. 7A to 7E show results of confirming expression of miR-136 in various ovarian cancer cell lines, wherein FIG. 7A shows results of comparing miR-135 expression of SKOV3 cell lines with that of anticancer agent-resistant SKpac cell lines, wherein the miR-136 expression levels of the paclitaxel-resistant SKpac-10, SKpac-13, SKpac-16, and SKpac-17 cells were significantly lower than the expression level of the SKOV3 cell lines (by 0.51-fold, p<0.005), and the test results are shown as mean±standard deviation, all analyses were repeated three times, and the values refer to means of the three independent tests, FIG. 7B shows results of the Pearson correlation analysis of the expression of Notch3 and miR-136 in various cancer cell lines, wherein the expression of miR-136 was inversely proportional to the Notch3 protein level expressed in ovarian cancer cell lines (n=5, X=−3.339, $R^2$=0.696, p=0.036), FIG. 7C shows results of confirming expression of miR-136 by performing qRT-PCR on a tissue sample (n=44) of an ovarian cancer patient, wherein, in each graph, the inner bars represent average values, and the average expression level of miR-136 in the ovarian cancer tissue was significantly lower than that of a control group (by 0.53-fold, p=0.0001), FIG. 7D shows the KaplaneMeier survival curve of 37 ovarian cancer patients according to the expression level of miR-136, wherein, the lower the expression of miR-136 (by <0.2-fold a normal control group), the shorter the survival period of the patient (log rank test, p=0.019), and FIG. 7E shows results of confirming the relationship between the expression of miR-136 and clinical stage progression (p=0.002) and benign lymph node metastasis (p=0.048) in ovarian cancer patients;

FIGS. 8A to 8C show results of confirming the relationship between anticancer agent resistance and miR-136 expression, wherein FIG. 8A shows results of evaluating viability of cells using CCK-8 after transfecting the cells with an miR-136 mimic, wherein, the viability of SKpac cells transfected with the miR-136 mimic in the presence of 40 nM and 80 nM PTX decreased by about 11% and about 21% as compared with the group treated with PTX alone, respectively, FIG. 8B shows results of a colony formation assay, wherein SKpac cells were seeded at a density of 300 cells/well and grown for 14 days, wherein the number of colonies formed on the cells transfected with the miR-136 mimic decreased by about 51.0% (p=0.007) in the absence of PTX and by about 34.8% (p=0.026) in the presence of PTX (40 nM) as compared with the group treated with PTX alone, and FIG. 8C shows results of a TUNEL assay, wherein apoptotic cells were detected by TUNEL staining and flow cytometric analysis, a proportion of the cells (33.2%) that became apoptotic due to being treated with a combination of the miR-136 mimic and PTX (40 nM) was higher than that of a PTX (40 nM)+miR-negative treatment group (4.7%), a proportion of the cells that became apoptotic due to being treated with a combination of the miR-136 mimic and PTX (80 nM) was increased as compared with that of a PTX (80 nM)+miR-negative treatment group (at 24 hours: 2.8% vs. 25.6%, p=0.028, at 48 hours: 4.6% vs. 49.6%, p=0.001);

FIGS. 9A to 9D show results of confirming changes of cancer cell lines resistant to an anticancer agent according to miR-136 expression, wherein FIG. 9A shows results of a spheroid formation assay, wherein the transfection with an miR-136 mimic reduced the number of spheroids by about 0.76-fold as compared with a control group, and a size of the spheroids was also reduced as compared with the control group, the group treated with PTX alone, and the PTX miR-negative treatment group, FIG. 9B shows results of performing qRT-PCR on SKpac cells transfected with miR-136, wherein the transfection with the miR-136 mimic reduced expression of ALDH1, CD24, CD133, and C-kit, which are cancer stem cell markers, FIG. 9C shows results of a wound healing assay, wherein ectopic expression of miR-135 inhibited migration in SKpac cells, and FIG. 9D shows results of a tube formation assay, wherein overexpression of miR-136 inhibited activation of cancer stem cells and limited migration and tube forming ability of SKpac cells;

FIGS. 10A to 10C show results of analysis of a population of ALDH1 (+) cells in various ovarian cancer cell lines, wherein FIG. 10A shows results of measuring ALDH1 enzyme activity in anticancer agent-sensitive SKOV3 cell lines and anticancer agent-resistant SKpac 16 cells by Aldefluor analysis, wherein DEAB is an ALDH1-specific inhibitor used to confirm a gating region, FIG. 10B shows results of comparing proportions of ALDH1(+) cells in SKOV3 cell lines and anticancer agent-resistant SKpac-12, SKpac-16, and SKpac-17 cell lines, FIG. 10C shows results of comparing expression of ALDH1 mRNA in FACS-sorted ALDH1 (+) and ALDH1 (−) cells, wherein all experimental data are shown as the average value of the results obtained from at least two independent experiments;

FIG. 11 shows results of confirming the relationship between anticancer agent-resistance and clinical-pathological parameters and ALDH1 (+), wherein A of FIG. 11 shows results of confirming ALDH1 mRNA expression in various anticancer agent-resistant SKpac sublines using qRT-PCR, wherein the relative expression level was normalized to the expression level of the parent SKOV3 cell line, B of FIG. 11 shows results of confirming ALDH1 expression levels in anticancer agent-resistant ovarian cancer tissues and anticancer agent-sensitive ovarian cancer tissues through qRT-PCR, and C of FIG. 11 shows results of confirming the relationship between ALDH1 mRNA expression and clinical stage progression;

FIGS. 12A and 12B show results of an analysis of microRNA expression patterns in ALDH (+) cells, FIG. 12A shows results of hierarchical clustering of miRNA expression profiles by miRNA array, the clustering showing a statistically significant (p<0.05) increase or decrease of ALDH1(+) as compared with ALDH(−), wherein the miRNA expression levels are indicated by color, and FIG. 12B shows results of verification of candidate miRNA using qRT-PCR, in which the bar graph shows expression of miRNA in flow cytometry-sorted ALDH(+) cells as compared with an average expression level of ALDH1, wherein all the experiments were repeated three times; and FIGS. 13A to 13D are results of confirming the relationship between anticancer agent-resistance and clinical-pathological parameters and ALDH1(+)-associated microRNA, wherein FIG. 13A shows results of comparing expression levels of ALDH1(+)-related microRNA in SKOV3 and anticancer agent-resistant SKpac cells, FIG. 13B shows results of confirming the expression level of ALDH1(+)-related microRNA in anticancer agent-resistant ovarian cancer tissues and anticancer agent-sensitive ovarian cancer tissues through qRT-PCR, FIG. 13C shows results of confirming the relationship between miR-503 expression and clinical stage progression, and FIG. 13D shows results of confirming the relationship between miR-27a expression and distant metastasis.

MODE OF DISCLOSURE

Hereinafter, the present invention will be described in more detail with reference to Examples. However, these examples are for illustrative purposes only and the scope of the present invention is not limited to these examples.

I. Effects According to Change of miR-150 Expression in Anticancer Agent-Resistant Cancer Cell Lines Example 1. Experiment Processes and Experiment Materials 1-1. Patients and Tissue Samples Samples from 58 patients with high-grade ovarian serous carcinoma (HGSC) were obtained from the archives of the Department of Pathology, CHA Bundang Medical Center. The tissues were fresh snap frozen for quantitative RT-PCR. As a control, ovarian benign serous tumor samples were used. Written informed consents were obtained from all patients prior to surgery, and all the experiments were approved by the Ethical Committee of the CHA Bundang Medical Center.

1-2. Ovarian Carcinoma Cell Lines

The human ovarian serous adenocarcinoma cell line (SKOV3) was obtained from American Tissue Type Collection (Manassas, Va., USA). Establishment of several paclitaxel (PTX)-resistant sublines (SKpac-10, SKpac-12, SKpac-13, SKpac-16, and SKpac-17) has been described previously. Briefly, SKpac cell lines were established by exposure of SKOV3 cells to a stepwise escalating concentration of PTX for more than 8 months. These cell lines were maintained in McCoy's 5A medium (Gibco/Life Technologies, Grand Island, N.Y., USA) supplemented with 10% fetal bovine serum, 100 U/ml penicillin, and 10 µg/ml streptomycin. Cultures were incubated at 37° C. in a humidified atmosphere containing 5% $CO_2$.

1-3. Transfection of miRNA Mimics

Pre miR-150 and pre miR-negative were purchased from Ambion (Life Technologies, Carlsbad, Calif., USA) and were transfected with Lipofectamine 3000 (Invitrogen/Life Technologies Carlsbad, Calif., USA) reagent according to the manufacturer's instructions.

1-4. Quantitative Real-Time PCR

Total RNA was extracted from fresh tissues and cell lines using a TRIzol reagent (Invitrogen/Life Technologies Carlsbad, Calif., USA) and reverse transcribed using specific miRNA primers and reagents from the TaqMan MicroRNA Reverse Transcription Kit (Applied Biosystems, Foster City, Calif., USA). The qRT-PCR for mature miRNAs was conducted using a Bio-Rad CFX96 real-time PCR detection system (Bio-Rad, Hercules, Calif.). All the PCRs were performed three times, and the probes and primers were those of hsa-miR-150-3p available from Applied Biosystems (cat NO: 4427975, ID:002637). The gene expression relative to RNU48 was calculated using the comparative threshold method ($2^{-\Delta\Delta C_t}$).

1-5. Luciferase Reporter Assay

The 3'UTR segments of Notch3 (human NOTCH3, NM_000435: chromosome 19:15270445-15271472; 1028 bp) were amplified by PCR from genomic DNA of SKpac-13, SKpac-16, and SKpac-17 cells. The putative binding sites for miR-150 within the 3'UTR of Notch3 were identified using the TargetScan algorithm (targetscan.org). The wild-type or mutated binding sites were cloned separately into the Nhel and Xhol sites of the pGL3-control vector (Promega, Mannheim, Germany). The pGL3-control (100 ng) and pRL-TK plasmid (5 ng; for normalization) were transfected into SKpac cells seeded in 24-well plates ($3 \times 10^4$ cells/well). Synthetic pre miR-150 (Ambion/Life Technologies, Carlsbad, Calif., USA) of 50 pmol was added to the reactions. Luciferase activity was measured on an Infinite 200pro series luminometer (Tecan Group, Zurich, Switzerland) using the Dual-Luciferase reporter assay system according to the manufacturer's instructions. All the experiments were performed three times and normalized to *Renilla* luciferase activity.

1-6. Spheroid-Forming Assay

Spheroid-forming assays were performed to verify the effect of miR-150 on cancer stem cell activation. SKpac-17 cells were transfected with pre miR-150 or pre miR-negative. Cells were plated in Ultra-Low-Attachment Surface 6-well culture plates (Corning, Action, MA, USA) in serum-free DEME/F12 medium (Gibco/Life Technologies, Grand Island, N.Y., USA) supplemented with 20 ng/ml epidermal growth factor (Gibco, Carlsbad, Calif., USA), 10 ng/ml basic fibroblast growth factor (Sigma-Aldrich, St. Louis, Mo., USA), 0.4% bovine serum albumin (Sigma-Aldrich, St. Louis, Mo., USA), and 5 μg/mL insulin (Sigma-Aldrich, St. Louis, Mo., USA) at a density of 1000 cells/cm². Spheroid formation (of 50 to 100 cells per spheroid) was assessed 7 days after seeding.

1-7. WST Assay

SKpac-12 or SKpac-17 cells were seeded at a density of $1 \times 10^5$ cells/well into 6-well plates. The next day, the cells were transfected with pre miR-150 and incubated for 48 hours. The transfected cells were then replated at a density of $1 \times 10^4$ cells/well into a 96-well culture plate. After 48 hours, a cell survival rate of the cells was measured by water-soluble tetrazoliumsalt (WST) assay according to the protocol of the Cell Counting Kit-8 (CCK, Dojindo, Japan). The absorbance was read at 450 nm using a microplate reader. All the WST experiments were performed three times and repeated at least three times.

1-8. Colony-Forming Assay

SKpac-16 or SKpac-17 cells were seeded at a density of $1 \times 10^5$ cells/well in 6-well plates. The next day, the cells were treated with pre miR-150 and incubated for 48 hours. The treated cells were then replated at 300 cells per well in a 6-well plate. After 14 days, colonies were fixed with 4% paraformaldehyde for 10 minutes, visualized using hematoxylin, and then the number of colonies containing 50 or more individual cells was counted.

1-9. TUNEL Assay for Apoptosis Analysis

TUNEL assays were performed after pre miR-150 transfection in SKpac-12 and SKpac-17. After 48 hours, apoptotic cells were analyzed using the In Situ Cell Death Detection kit (Roche, Mannheim, Germany). $2 \times 10^7$ cells were fixed with 75% ethanol for 2 hours at −20° C. The cells were washed twice with PBS and incubated with 0.1% Triton X-100 and 0.1% sodium citrate for 2 minutes on ice. After washing twice with PBS, the cells were incubated with a TUNEL-labelling mixture for 1 hour at 37° C. in the dark. The samples were washed twice with PBS and analyzed by fluorescence activated cell sorting (FACS) (Becton Dickinson, Franklin Lakes, N.J., USA).

1-10. Wound Healing Assay

Would healing assays were performed after pre miR-150 transfection in SKpac-12 and SKpac-17 cells. The cells were seeded into 24-well tissue culture plates and grown to confluence. An acellular area was created by scraping the cell surface using a sterile yellow pipette tip. The wounded monolayer was washed twice with PBS to remove floating cell debris. The monolayer was then incubated in cell culture medium and the rate of defect closure was monitored for 16 hours. Individual cells were quantified as an average of at least five fields for each experiment.

1-11. Angiogenesis Assay

Matrigel (BD Biosciences, California, USA) was placed into flat-bottom, 96-well plate and polymerized for 1 hour at 37° C. HUVECs incubated in M199 containing 1% FBS were harvested after trypsin treatment, resuspended in M199, plated onto the layer of Matrigel at a density of $1 \times 10^4$ cells/well, and the supernatant of SKpac-17 cells transfected by pre miR150 was added. After 24 hours, 48 hours, and 72 hours, tube formation was observed.

1-12. Western Blot

Cells were lysed by protein extraction buffer (Pro-Prep, iNtRON Biotechnology, Korea) on ice for 30 minutes. After centrifugation at 4° C., 13,000 rpm for 15 minutes, the protein was measured with the Bradford assay (Sigma, Saint Louis, USA) form the supernatant. Same amounts of total protein were separated by 10% SDS-PAGE and transferred to nitrocellulose membranes (Millipore Co., Bedford, Mass., USA). After blocked with 5% skim milk for 1 hour at room temperature, the membranes were incubated overnight at 4° C. in primary antibody, followed by 1:5,000 HRP conjugated anti-mouse antibody or 1:5,000 anti-rabbit secondary antibody incubation for 1 hour at room temperature. Next, the bands of membranes were visualized by an enhanced luminol-based chemiluminescence (ECL) detection kit (Bio-Rad Laboratories, Hercules, Calif., USA). The quantification of protein was done by densitometric digital analysis of protein bands using the Image Lab™ Software (Bio-Rad Laboratories, Hercules, Calif., US) and ChemiDoc™ XRS+. Equal loading was confirmed by reprobing the membrane with beta-actin.

1-13. Statistical Analysis

Statistical analyses were performed using SPSS Software version V20.0.0 (IBM SPSS). The Student's t-test was used to determine the statistical significance between chemoresistant cell lines and controls. For each result, significant changes within the 95% confidence interval ($P < 0.05$) were analyzed.

Example 2. Confirmation of Expression Change of miR-150 in High-Grade Serous Ovarian Cancer (HGSC) and PTX-Resistant Ovarian Cancer Cells (SKpac Cells)

In this Example, the expression of miR-150 in each sample was analyzed by qRT-PCR to compare the relative levels of miR-150 in benign ovarian serous tumor (BT) and HGSC samples (OC).

Figure 1:
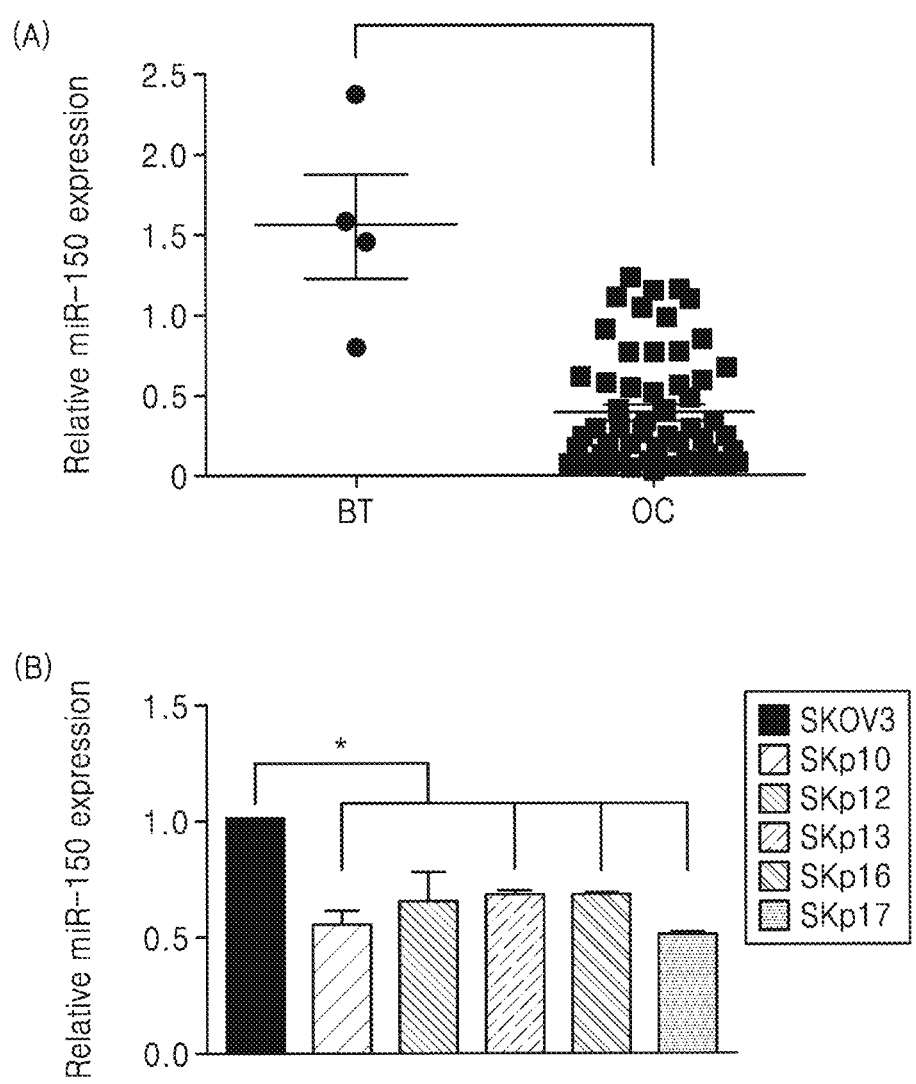
FIG. 1 shows results of measuring expression of miR-150 in samples of benign ovarian serous tumor (BT) and high-grade ovarian serous carcinoma (OC) using quantitative reverse transcription polymerase chain reaction (qRT-PCR), wherein A of FIG. 1 shows that an expression of miR-150 in the high-grade ovarian serous carcinoma (OC) was significantly reduced by about 0.2-fold as compared with the benign ovarian serous tumor (BT) (P<0.05), and B of FIG. 1 confirms a relative expression level of miR-150 in PTX-resistant SKpac cells as compared with parent SKOV3 ovarian cancer cells, where the expression level of miR-150 in PTX-resistant SKpac cells was significantly downregulated by about 0.5 to 0.6-fold as compared with the parent SKOV3 ovarian cancer cells (P<0.05)

As a result, as shown in A of FIG. 1, it was observed that the expression level of miR-150 was significantly down-regulated by 0.2-fold in HGSC cases compared with BT cases ($P < 0.001$). Also, to investigate whether endogenous miR-150 levels are associated with chemoresistance, the expression level of miR-150 was quantified using real-time qRT-PCR analysis of RNAs isolated from SKOV3 and SKpac cells. As a result, as shown in B of FIG. 1, the miR-150 expression was significantly lower in PTX-resistant SKpac cells (SKpac-10, SKpac-12, SKpac-13, SKpac-16, and SKpac-17) than that in SKOV3 parental cancer cells ($P < 0.05$).

Example 3. Confirmation of Action Mechanism of miR-150 on Regulation of Notch3 Expression A luciferase reporter assay was performed to determine whether miR-150 directly targets Notch3 in SKpac-13, SKpac-16, and SKpac-17 cell lines. In this regard, SKOV3 cells were co-transfected with a pGL3 vector containing the firefly luciferase reporter upstreaming of the 3'UTR of Notch3, a pRL-TK vector expressing *Renilla* luciferase (as a control), and 50 pmol of pre miR-150 or a control miRNA.

Figure 2:
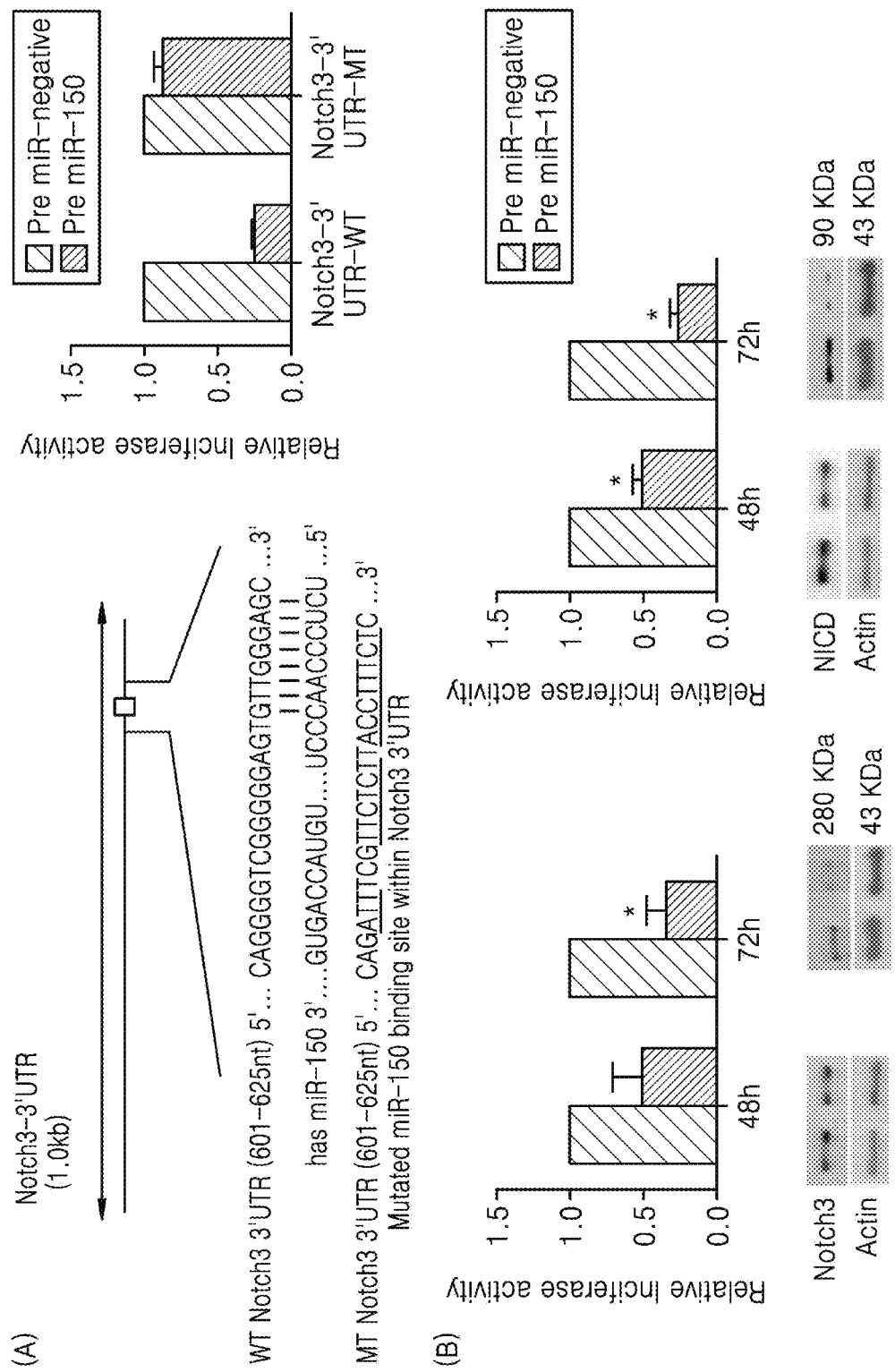
FIG. 2 shows results of confirming whether miR-150 directly targets Notch3, which is a primary oncogene of ovarian cancer, by performing a luciferase reporter assay, wherein A of FIG. 2 shows a putative miR-150 target site and a mutant thereof in 3'UTR of Notch3 (left) and results of comparing effects of miR-150 of a reporter gene having a wild type (WT) or a mutated type (MT) of Notch3-3'UTR in SKpac cells to luciferase activity (right), and B of FIG. 2 confirms effects of overexpression of miR-150 on expression of Notch and NICD3, where significant expression reduction of Notch3 and NICD was observed at 48 hours and 70 hours in the pre miR-150 transfected SKpac cell line.

As a result, as shown in A of FIG. 2, luciferase activity in the cells transfected with pre miR-150 was significantly lower (25±5%) than that in the cells transfected with the control miRNA, whereas pre miR-150 transfection showed no significant effect on luciferase activity of reporter construct containing mutant NOTCH3 3'UTR.

Also, to confirm that the protein expression of Notch3 and NICD is regulated by miR-150, in this Example, the gain-of-function analysis by forced expression of endogenous miR-150 with pre miR-150 transfection in SKpac cells was performed, and pre miR-negative was used as a negative control. MiR-150 was stably overexpressed with a pre miR-150 transfection in SKpac cells resulting in a 5-fold increase in miR-150 expression (not shown). Also, as shown in B of FIG. 2, forced expression of miR-150 reduced the levels of both Notch3 and NICD to 34% to 50% and 27% to 52%, respectively, in SKpac-12 and SKpac-17 cells. Collectively, it may be known that miR-150 targets 3'UTR of Notch3 and directly regulates Notch3 and NICD expression in SKpac cells.

Example 4. Confirmation of Effect of miR-150 on Activity of Cancer Stem Cells In order to verify the effect of miR-150 transfection on cancer stem cells (CSCs) activation, a spheroid-forming assay was performed on paclitaxel-resistant SKpac cells in this Example, and alteration of mRNA of the stemness genes was detected using real-time RT-PCR.

As a result, as shown in A of FIG. 3, the number of spheroids after pre miR-150+PTX transfection decreased significantly to about 0.38-fold relative to a group treated with PTX alone (pre miR-150) or a group treated with PTX+miR-negative (pre miR-negative+PTX). Also, in SKpac cells, when PTX treatment and pre miR-150 transfection are combined (pre miR-150+PTX), the size of spheroids was also significantly reduced relative to a group treated with PTX alone or a group treated with PTX+miR-negative. That is, it may be known that while the PTX alone-treatment induced no changes in spheroid formation, when the cells were treated with pre miR-150 in addition to PTX, CSC activation in PTX-resistant ovarian cancer cells decreased. Also, as shown in B of FIG. 3, after transfection with pre miR-150, the mean mRNA expression levels of NOTCH3, ALDH1, CD24, CD133, and c-Kit significantly reduced to 0.67-, 0.57-, 0.70-, 0.70-, and 0.51-fold, respectively (P=0.046, P=0.019, P=0.012, P=0.031, P=0.002, respectively) relative to control. This experiment result indicates that miR-150 plays an important role in regulating activity of CSCs.

Example 5. Confirmation of Anti-Tumor Effect According to Upregulation of miR-150

If PTX resistance or tolerance is related to miR-150 downregulation, an artificial augmentation of miR-150 expression levels might modulate PTX sensitivity. To investigate the effect of pre miR-150 on cancer cell proliferation as a single agent or in combination with PTX chemotherapeutics on SKpac cells (SKpac-12 and SKpac-17 cells), cell viability was evaluated using WST assays. In five separate WST assay experiments, SKpac cells were subjected to therapy with one of pre miR-150 alone-treatment (pre miR-150), PTX alone-treatment (PTX), pre miR-negative alone-treatment (pre miR-negative), miR-150-negative-treatment in combination with PTX (pre miR-negative+PTX), and pre miR-150-treatment in combination with PTX (pre miR-150+PTX).

As a result, as shown in FIG. 4A, when the cells were treated with pre miR-150 transfection in the presence of 40 nM PTX, the number of SKpac cells decreased by 34% at 48 hours, relative to the cells treated with PTX alone. Administration of pre miR-150 showed partial decrease in tumor cell viability at 48 hours. In all analyzed cases, an enhanced anti-tumor activity was found in SKpac cells treated with the combination of pre miR-150 and PTX, compared with those treated with PTX alone and PTX+pre miR negative.

Also, to investigate the growth inhibition effect, i.e., the anti-proliferative effect, of SKpac cells according to the treatment with pre miR-150 alone or the combination of PTX and pre miR-150, colony forming assays were performed. As a result, as shown in FIG. 4B, both pre miR-150 alone and the combination of PTX and pre miR-150 treatment decreased the cell proliferation by about 44% and 43%, respectively, relative to the cells treated with PTX alone or pre miR-negative+PTX and significantly inhibited clonal growth of SKpac cells (86%, *P<0.05). Collectively, it may be known that miR-150 has an anti-proliferative effect on PTX-resistant SKpac cells either when used alone or in combination with PTX.

In addition, to determine the effect of miR-150 on apoptosis, the SKpac cells (SKpac-12, SKpac-16, and SKpac-17) were transfected with pre miR-150, and then a TUNEL assay was performed on the cells. As a result, as shown in FIG. 4C, when the cells were transfected with pre miR-150 alone or with pre miR-150 and 40 nM PTX treatment, the apoptosis each increase by about 14.4% and 40.6%, respectively, as compared with those of the PTX alone treatment or PTX+pre miR-negative treatment (3.5% and 4.3%, respectively, *P<0.05). Collectively, the pre miR-150 transfection by itself or increased a sensitivity of tumor cells with respect to PTX and thus decreased tumor cell proliferation and induced apoptosis in PTX-resistant ovarian cancer cells.

Example 6. Confirmation of Effect of miR-150 on Cell Migration and Angiogenesis Cell migration and angiogenesis are important factors that influence tumor progression and metastasis. In this Example, a wound healing assay and a tube formation assay were performed to examine the effect of pre miR-150 on cell migration and the effect on angiogenesis, respectively.

As a result, as shown in FIG. 5A, cell migration of pre miR-150 (40 nM) treatment significantly decreased as compared with those of the PTX alone treatment or pre miR-negative+PTX treatment (28.7% and 36%, respectively, P<0.05). Also, as shown in FIG. 5B, the pre miR-150 transfected cells reduced tube formation by about 61.1% at 24 hours, about 50.5% at 48 hours, and 42.6% at 72 hours, relative to control HUVECs in the pre miR-negative cells (*P<0.05). On the other hand, the reduction effect was not observed when cells were treated with PTX alone or with pre miR-negative+PTX. That is, these results indicate that pre miR-150 transfection significantly inhibits tumor cell migration and angiogenesis in PTX-resistant ovarian cancer cells.

Example 7. Confirmation of Effect of miR-150 on Expression of Functional Protein In this example, change in expression of Notch3 downstream target protein in SKpac-13 cells according to pre miR-150 treatment was analyzed.

As a result, as shown in FIG. 6A, the expression of Notch3 downstream target protein including NICD3 and Hey2 was further downregulated by the pre miR-150 transfection. At 24 hours after the transfection, levels of NICD3 and Hey2 were significantly reduced by about 0.56-fold and 0.67-fold, respectively, as compared to that of a control (P=0.05 and P<0.05, respectively), whereas the transfection did not have much influence on expression of Hes1 and Hey1. These results indicate that miR-150 selectively regulates expression of Notch3 downstream protein.

Also, the expression of proteins, including DNA-PK, pS6, S6, NF-κB, p21, and p27, associated with cell survival and cell cycles in SKpac-13 cells treated with pre miR-150 were analyzed. As shown in FIG. 6B, after 24 hours after transfection, expression levels of DNA-PK, pS6, S6, cyclin D3, p21, p27, and NF-κB were significantly decreased (DNA-PK: 0.18-fold; PS6: 0.25-fold; S6: 0.27-fold relative to a control), and those of cell cycle proteins were also downregulated (cyclin D3: 0.36-fold; p21: 0.4-fold; p27: 0.08-fold; NF-κB: 0.10-fold relative to a control) (*P<0.05).

As shown in FIG. 6C, treating the proteins related with apoptosis with pre miR-150 also significantly decreased the expression levels of the anti-apoptotic proteins, such as BCL-W, BCL-2, and BCL-XL, by about 0.51-fold, 0.42-fold, and 0.51-fold, respectively, relative to a control (P=0.002, P=0.018, and P=0.094, respectively). The levels of five pro-apoptotic proteins, Bad, Bak, Bim, Bid, and Bax, were increased by about 3.71-fold, 4.57-fold, 2.83-fold, 1.41-fold, and 1.23-fold, respectively, relative to a control. These results indicate that miR-150 may induce apoptosis by inhibition of anti-apoptotic genes and increase of apoptotic genes in the PTX-resistant ovarian cancer cells.

II. Effect According to Change in Expression of miR-136 in Anticancer Agent-Resistant Cancer Cell Lines Example 1. Confirmation of miR-136 Expression in Various Ovarian Cancer Cell Lines To evaluate the relationship between miR-136 expression and anticancer agent-resistance of ovarian cancer cells and Notch3 protein expression, in this Example, PCRs were performed on SKOV ovarian cancer cell lines and previously established PTX-resistant sublines, SKpac-10, SKpac-13, SKpac-16, and SKpac-17. As previously reported, the expression level of Notch3 protein was significantly high in the PTX-resistant ovarian cancer cells as compared with the level of the parent SKOV3 cells. Also, as shown in FIG. 7A, the miR-136 expression levels in the PTX-resistant SKpac-10, SKpac-13, SKpac-16, and SKpac-17 cells, which overexpress Notch3, were significantly lower than that of the SKOV3 cells (in average by 0.51-fold, p<0.05). Also, to confirm whether miR-136 regulates Notch3, the relationship between expression levels of the Notch3 protein and miR-136 in various ovarian cancer cell lines (SKOV3 and SKpac-10, SKpac-13, SKpac-16, and SKpac-17) were investigated. As a result, as shown in FIG. 7B, the miR-136 expression was reversely proportional to the Notch3 protein level expressed in the ovarian cancer cell lines (Pearson's correlation, X=−3.339, $R^2$=0.696, p=0.036). To further evaluate clinical role of miR-136 in the ovarian cancer patients (OSCs), qRT-PCR was performed on series of ovarian cancer patient tissue samples (n=44) to measure miR-136 expression. As a result, as shown in FIG. 7C, the miR-136 expression in the patients was observed about 0.53-fold lower than that of tissues of a normal control (p<0.001). Next, 38 cases available to confirm survival data were evaluated to investigate the relationship between miR-136 expression and the survival rate of a patient. As a result, as shown in FIG. 7D, it was confirmed that in the Kaplane-Meier curve, survival rates of patients having low expression of miR-136 (about <0.2 fold compared to a normal control) were significantly lower than those of patients having high expression of miR-136 (about >0.2 fold compared to a normal control) (log rank, p=0.019). Also, as shown in FIG. 7E, the downregulation of miR-136 (about <0.2 fold compared to a normal control) was related to clinical stage progression (III-IV, p=0.002) and benign lymph node metastasis (p=0.048). The experiment results indicate that low expression of miR-136 is associated with poor prognosis in ovarian cancer patients.

Example 2. Confirmation of Relationship Between Anticancer Agent-Resistance and miR-136 Expression In order to investigate the role of miR-136 in the anticancer agent-sensitivity and proliferation activity of PTX-resistant SKpac cells, cell survival rate, cell proliferation, and apoptosis analyses were performed on the SKpac cells transfected by miR-136 mimics. The treatment of miR-136 mimics and PTX (40 nM and 80 nM) on the SKpac cells overexpressing Notch3 significantly decreased the cell viability 24 hours after the treatment (by 11% and 21%, p=0.5 and p=0.02, respectively), and, as shown in FIG. 8A, the results measured in a WST assay shows that the PTX-alone treatment had no influence on the cell viability. Also, as shown in FIG. 8B, the miR-136 mimics alone or a combination of miR-136 mimics and PTX inhibited colony forming capability of the SKpac cells by about 51% and 36%, respectively, as compared with control cells transfected by cells treated with miR-negative and cells treated with PTX (p<0.05). In addition, to confirm whether overexpression of miR-136 increases cell toxicity induced by PTX, degrees of apoptosis were evaluated using a TUNEL analysis. As a result, as shown in FIG. 8C, more cases of apoptosis were observed in the cells transfected with miR-136 mimics than that of the control cells transfected with miR-negative at 48 hours after the treatment (1.63% vs. 7.03%, p=0.05), and the combining treatment of miR-136 mimics and PTX (40 nM or 80 nM) increased apoptosis rates as compared with those of a group treated with PTX (40 nM)+miR-negative (at 48 hours: 4.7% vs. 33.2%, p=0.049) and a group treated with PTX (80 nM)+miR-negative (at 24 hours: 2.8% vs. 25.6%, p=0.028; at 48 hours: 4.6% vs. 49.6%, p=0.001). In collection of these experiment results, it may be known that the overexpression of miR-136, when used alone or in a combination with PTX, decreases cell viability and cell proliferation of anticancer agent-resistant ovarian cancer cells and increases apoptosis.

Example 3. Change in Anticancer Agent-Resistant Cancer Cell Lines According to miR-136 Expression In order to investigate the role of miR-136 in activation of cancer stem cells with respect to SKpac cells, a spheroid formation assay was performed. As a result, overexpression of miR-136 in SKpac cells that did not react to the PTX alone treatment inhibited spheroid formation. In particular, as shown in FIG. 9A, PTX+miR-136 mimic-transfected cells formed less and smaller spheroids as compared with those formed by PTX-miR-negative mimic-transfected cells corresponding to the PTX+miR-136 mimic-transfected cells. Also, as shown in FIG. 9B, as a result of evaluating mRNA expression of ALDH1, CD24, CD133, and C-kit, which are CSC markers, the transfection by miR-136 mimics expressed these markers by about 0.64-fold, 0.84-fold, 0.76-fold, and 0.46-fold, respectively, as compared with that of the control group cells and thus reduced the expression levels of the markers (p=0.013, p=0.013, p<0.01, and p=0.075, respectively). Also, in order to investigate the role of miR-136 in regulation of migration activity and angiogenesis of SKpac cells, a wound healing assay and a tube forming assay were performed. As a result of the wound healing assay, as shown in FIG. 9C, at 6 hours after the analysis, the average number of migrated cells among the miR-136 mimic-transfected cells was observed as relatively low (P=0.003) as about 74.5% as compared to that of miR-control-transfected cells, and thus it was confirmed that ectopic expression of miR-135 inhibits migration of SKpac cells. As a result of the tube forming assay, as shown in FIG. 9D, since tube formation in HUVECs treated with the supernatant derived from miR-136 mimic-transfected cells significantly decreased as compared to that of the case by miR-control-transfected cells (at 48 hours: 43.6%, at 72 hours: 45.0%), it was confirmed that overexpression of miR-136 inhibits tube formation of SKpac cells. These experiment results indicate that overexpression of miR-136 inhibits activation of CSCs and limits migration and tube forming capability of SKpac cells.

III. Effect According to Change in Expression of ALDH1 (+)-Related microRNA in Anticancer Agent-Resistant Cancer Cell Lines Example 1. Population Analysis of ALDH1 (+) Cells in Various Ovarian Cancer Cell Lines In this Example, an ALDH1(+) cell group, which is a potential cancer stem cell marker, in ovarian cancer cell lines (SKOV3, A2780, and OVCAR 3), PTX-resistant sublines (SKpac-12, SKpac-16, SKpac-17, A2780pac, and A2780cis), primary tumor cells (SCN1-7) was investigated. As a result, as shown in Table 1, it was confirmed that ALDH1(+) cells were present at a proportion of about 0.9% to 17.2% in the ovarian cancer cell lines and about 0.4% to 4.0% in the primary tumor cells.

TABLE 1

| Cells | % ALDH1 (+) cell |
|---|---|
| SKOV3 | 0.9 ± 0.2 |
| Skpac | 4.46 ± 0.71 |
| A2780 | 1.66~7 |
| A2780pac | 7.96 |
| A2780cis | 2.25 |
| Ovcar3 | 17.16 |
| SCN 1 | 0.4 |

TABLE 1-continued

| Cells | % ALDH1 (+) cell |
|---|---|
| SCN 2 | 0.5 |
| SCN 3 | 0.9 |
| SCN 4 | 3.96 |
| SCN 5 | 1.9 |
| SCN 6 | 1.35 |
| SCN 7 | 4.05 |

SCN, primary ovarian cancer cells.

As shown in FIGS. 10A and 10B, a proportion of ALDH (+) population in the anticancer agent-resistant SKpac cells according to the FACS analysis (4.46±0.71%) significantly increased as compared with that of the parent SKOV3 cells (0.9±0.2%), and thus the relationship between ALDH(+) cells and anticancer agent-resistance was confirmed in this regard. Also, to confirm whether FACS-sorted ALDH(+) cells increase expression of ALDH-1, qRT-PCR was performed on ALDH1 mRNA. As a result, as shown in FIG. 10C, it was confirmed that the FACS-sorted ALDH(+) population had about 2.5-fold higher expression of ALDH1 mRNA as compared with that of ALDH1(−) population.

Example 2. Confirmation of Relationship Between Anticancer Agent-Resistance and Clinical-Pathological Parameters and ALDH1(+)

In this Example, qRT-PCR was performed to investigate expression of ALDH1 mRNA in ovarian cancer cells and 34 ovarian cancer tissue samples. ALDH1 mRNA expression levels of chemoresistant Skpac cell lines were compared with those of chemosensitive SKOV3 cell lines. As a result, as shown in A of FIG. 11, the ALDH1 mRNA expression levels of anticancer agent-resistant Skpac cell lines significantly increased by about 12-fold to about 124-fold as compared with those of the SKOV3 cell lines. Also, a relative expression level of ALDH1 mRNA was obtained by comparing with normal epithelial cells to compare expression levels between a chemoresistant group and a chemosensitive group in human ovarian cancer tissue samples. As shown in B of FIG. 11, the expression of ALDH1 mRNA in the chemoresistant group (11-fold) significantly increased as compared with that in the chemosensitive group (4.29-fold). In addition, to evaluate the role of ALDH1 in ovarian cancer, the relationship between expression of ALHA1 mRNA and clinical-pathological parameters such as clinical stage progression was confirmed. In this comparison, patients were classified into an ALDH1 high-expression group (2-fold or higher) and an ALDH1 low-expression group (2-fold or lower). As a result, as shown in C of FIG. 11, it was confirmed that high expression of ALDH1 is significantly related to clinical stage progression (p=0.019).

Example 3. Analysis on Expression Pattern of MicroRNA in ALDH(+) Cells

In this Example, an Affymetrix GeneChip microarray analysis including 4,560 human precursors and mature miRNA oligonucleotide probes was performed to characterize the mRNA expression profile of ALDH 1(+) cells. As a result, as shown in Table 2 and FIG. 12A, the total of 6 types of miRNA being overexpressed by about 1.5-fold or more in the ALDH1(+) cells as compared with those of ALDH1(−) cells were confirmed (miR-424 [1.98-fold], miR-346 [1.95-fold], miR-503 [1.86-fold], miR-27a [1.66-fold], miR-23b [1.53-fold], and miR-27b [1.50-fold]).

TABLE 2

| Name | Absolute fold change | P-value | Chromosome | Putative target genes |
| --- | --- | --- | --- | --- |
| hsa-miR-424 | 1.98 | 0.02 | Xq26.3 | WEE1, CDCA4, USP15, LATS2, HIPK2 |
| hsa-miR-346 | 1.95 | 0.01 | 10q23.2 | PTPN18, LIF |
| hsa-miR-503 | 1.86 | 0.05 | Xq26.3 | CDCA4 |
| hsa-miR-27a | 1.66 | 0.03 | 19p13.13 | GSPT1, CDS1, TAB3, SFRP1, MDM4, PRKCB, SESN2, FOSB, SMAD2 |
| hsa-miR-23b | 1.53 | 0.02 | 9q22.32 | APAF1, PPP2R5E, PPP1CB, PPIF, REPS2, CHUK |
| hsa-miR-27b | 1.50 | 0.03 | 9q22.32 | GSPT1, CDS1, TAB3, PRKCB |

The target genes presented are predicted using the TargetScan (http://www.targetscan.org) and PicTarVert (http://pictar.mdc-berlin.de) softwares.

In the ALDH(+) cells, miRNA downregulating the expression was not confirmed. Also, to confirm the microarray analysis results, real-time RT-PCR was performed and expression of the total of 6 types of miRNAs in the ALDH1 (+) cells and ALDH1(−) cells were analyzed. As a result, as shown in FIG. 12B, the results similar to the microarray analysis result were confirmed (miR-424 [1.62-fold], miR-346 [3.25-fold], miR-503 [1.66-fold], miR-27a [2.08-fold], miR-23b [1.98-fold], and miR-27b[3.09-fold]).

Example 4. Confirmation of Relationship Between Anticancer Agent-Resistance and Clinical-Pathological Parameters and ALDH1(+)-Related MicroRNA In this Example, qRT-PCR was performed on ovarian cancer cells and 34 ovarian cancer tumor samples, and their miRNA expression was investigated to evaluate influence of miRNA of Example 3 on chemoresistance of ovarian cancer. The miRNA expression levels of chemoresistant SKpac cell lines were compared with levels of chemosensitive SKOV3 cell lines. As a result, as shown in FIG. 13A, among the miRNAs, expression levels of miR-23b (2.8-fold, p=0.039), miR-27b (3.5-fold, p=0.007), miR-346 (2.7-fold, p=0.02), and miR-503 (2.2-fold, p=0.049) in SKpac cell lines were observed significantly higher compared with those of the SKOV3 cell lines. Also, a relative expression level of the mRNA was obtained by comparing with normal epithelial cells to compare expression levels between a chemoresistant group and a chemosensitive group in human ovarian cancer tissue samples. As a result, as shown in FIG. 13B, the expression levels of miR-23b (3.5-fold vs. 0.6-fold p=0.037), miR-27b (5.5-fold vs. 1.6-fold, p=0.040), and miR-424 (2.0-fold vs. 0.7-fold, p=0.047) were observed significantly high in the chemoresistant group as compared with those in the chemosensitive group. In addition, to evaluate the role of the miRNA in ovarian cancer, the relationship between expression of the mRNA and clinical-pathological parameters such as clinical stage progression and distant metastasis was confirmed. For the comparison, patients were classified into a miRNA high-expression group (1.5-fold or higher) and a miRNA low-expression group (1.5-fold or lower). As a result, as shown in FIGS. 13C and 13D, it was confirmed that high expression of miR-503 is significantly related to clinical stage progression (stages III and IV, p=0.033) and that high expression of miR-27a is significantly related to distant metastasis (p=0.046).

The invention claimed is:

1. A method of treating a taxane anticancer agent-resistant cancer, the method comprising: administering a pharmaceutical composition comprising miR-150 as an active ingredient to the individual.

2. The method of claim 1, wherein the miR-150 is designed to be accommodated in viral or non-viral vectors.

3. The method of claim 1, wherein the taxane anticancer agent is one selected from the group consisting of paclitaxel, docetaxel, larotaxel, cabazitaxel, and a combination thereof.

4. The method of claim 1, wherein the cancer is one selected from the group consisting of ovarian cancer, liver cancer, colon cancer, cervical cancer, kidney cancer, gastric cancer, prostate cancer, breast cancer, brain tumor, lung cancer, uterine cancer, colon cancer, bladder cancer, and pancreatic cancer.

5. The method of claim 1, wherein the pharmaceutical composition further comprises miR-136.

6. The method of claim 1, wherein the pharmaceutical composition further comprises an agent that inhibits an expression level of one selected from the group consisting of miR-23b, miR-27b, miR-326, miR-424, miR-503, and a combination thereof.

\* \* \* \* \*